US006322963B1

United States Patent
Bauer

(10) Patent No.: US 6,322,963 B1
(45) Date of Patent: Nov. 27, 2001

(54) SENSOR FOR ANALYTE DETECTION

(75) Inventor: Alan Joseph Bauer, Jerusalem (IL)

(73) Assignee: Biosensor Systems Design., Inc., Cedarhurst, NY (US)

( * ) Notice: Subject to any disclaimer, the term of this patent is extended or adjusted under 35 U.S.C. 154(b) by 0 days.

(21) Appl. No.: 09/701,906
(22) PCT Filed: Jun. 10, 1999
(86) PCT No.: PCT/IL99/00309
§ 371 Date: Dec. 5, 2000
§ 102(e) Date: Dec. 5, 2000
(87) PCT Pub. No.: WO99/66322
PCT Pub. Date: Dec. 23, 1999

Related U.S. Application Data

(63) Continuation-in-part of application No. 09/110,686, filed on Jul. 7, 1998, now Pat. No. 6,096,497.

(30) Foreign Application Priority Data

Jun. 15, 1998 (IL) .......................................................... 124903
Aug. 19, 1998 (IL) .......................................................... 125720
Nov. 12, 1998 (IL) .......................................................... 127019
May 4, 1999 (IL) .......................................................... 129754

(51) Int. Cl.[7] ............................... C12Q 1/00; C12M 1/00; C12M 1/34
(52) U.S. Cl. ...................... 435/4; 435/287.1; 435/289.1; 435/817; 435/283.1; 204/403; 204/164; 204/193; 205/81; 205/372; 422/82.01; 422/50
(58) Field of Search ....................... 435/4, 287.1, 289.1, 435/817, 283.1; 204/403, 164, 193; 205/81, 372; 422/82.01, 50

(56) References Cited

U.S. PATENT DOCUMENTS 4,822,566   4/1989   Newman ................................ 422/68

(List continued on next page.)

FOREIGN PATENT DOCUMENTS

| 441 120 | 8/1991 | (EP) . |
| WO 97/01092 | 1/1997 | (WO) . |
| WO 97/22875 | 6/1997 | (WO) . |
| WO 97/41425 | 11/1997 | (WO) . |
| WO 98/10289 | 3/1998 | (WO) . |

OTHER PUBLICATIONS

Radmacher, Manfred et al. *Direct Observation of Enzyme Activity with the Atomic Force Microscope.* Science 265:1577, Sept. 9, 1994.

(List continued on next page.)

Primary Examiner—Louise N. Leary
(74) Attorney, Agent, or Firm—Arthur S. Bickel

(57) ABSTRACT

A sensor for detecting analytes is described. Analyte presence or concentration is determined through measurement of changes in induced electromotive force, current or other electrical property in a base member during analyte exposure to the sensor. According to one class of embodiments, the present device immobilizes natural or synthetic macromolecules sufficiently close to an electrically-conductive base member to insure that any alteration in the motion and/or electrostatic fields of the macromolecules during interaction with a predetermined analyte will induce an increased electromotive force in the base member.

17 Claims, 9 Drawing Sheets

U.S. PATENT DOCUMENTS

| | | | |
|---|---|---|---|
| 4,839,017 | 1/1989 | Isao et al. | 435/4 |
| 4,916,075 | 4/1990 | Malmros et al. | 435/291 |
| 5,156,810 | 10/1992 | Ribi et al. | 422/82.01 |
| 5,264,103 | 11/1993 | Yoshioka et al. | 204/403 |
| 5,482,855 | 1/1996 | Kenshi et al. | 435/4 |
| 5,491,097 | 2/1996 | Ribi et al. | 436/518 |
| 5,543,326 | 8/1996 | Heller et al. | 436/817 |
| 5,585,646 | 12/1996 | Kossovsky et al. | 257/40 |
| 5,605,662 | 2/1997 | Heller et al. | 435/4 |
| 5,620,854 | 4/1997 | Holzrichter et al. | 435/6 |
| 5,719,033 | 2/1998 | Ackley et al. | 435/7.92 |
| 5,783,056 | 7/1998 | Hampp et al. | 204/403 |
| 6,096,497 * | 8/2000 | Bauer | 435/4 |

OTHER PUBLICATIONS

Patel et al., *Immobilization of Protein Molecules onto Homogeneous and Mixed Carboxylate–Terminated Self–Assembled Monolayers*, Langmuir 6485–6490, 1997.

Bardea, Amos et al., *NAD+ Dependent Enzyme Electrodes: Electrical Contact Cofactor–Dependant Enzymes and Electrodes*. J. Am. Chem Soc. 119:9114–91119, 1997.

Willner, Itamar et al., *Assembly of Functionalized Monolayers of Redox Proteins on Electrode Surfaces: Novel Bioelectric and Optobioelectric Systems*. Biosensors & Bioelectronics 12, No. 4, pp. 337–356, 1997.

Souteyrand E. et Al., Direct Detection of Biomolecules by Electrochemical Impedance Measurements. Sensors and Actuators B. vol. B20, No. 1 May 1, 1994–05–01. pp. 63–69; abstract, figures 1,2.

* cited by examiner

SENSOR FOR ANALYTE DETECTION

This Application is a 371 of PCT/IL99/00309 filed Jun. 10, 1999, which is a CIP of Ser. No. 09/110,686 filed Jul. 7, 1998 as U.S. Pat. No. 6,096,497.

This invention pertains to a sensor and method for detecting or quantifying analytes. More particularly the present invention is directed to the detection of analytes by interaction thereof with an immobilized macromolecular entity and the analysis of certain induced electromagnetic effects that are produced as a result of such interactions.

Chemical and biological sensors are devices that can detect or quantify analytes by virtue of interactions between targeted analytes and macromolecular binding agents such as enzymes, receptors, DNA strands, heavy metal chelators, or antibodies. Such sensors have practical applications in many areas of human endeavor. For example, biological and chemical sensors have potential utility in fields as diverse as blood glucose monitoring for diabetics, detection of pathogens commonly associated with spoiled or contaminated food, genetic screening, and environmental testing.

Chemical and biological sensors are commonly categorized according to two features, namely, the type of material utilized as binding agent and the means for detecting an interaction between binding agent and targeted analyte or analytes. Major classes of biosensors include enzyme (or catalytic) biosensors, immunosensors and DNA biosensors. Chemical sensors make use of synthetic macromolecules for detection of target analytes. Some common methods of detection are based on electron transfer, generation of chromophores, or fluorophores, changes in optical or acoustical properties, or alterations in electric properties when an electrical signal is applied to the sensing system.

Enzyme (or catalytic) biosensors utilize one or more enzyme types as the macromolecular binding agents and take advantage of the complementary shape of the selected enzyme and the targeted analyte. Enzymes are proteins that perform most of the catalytic work in biological systems and are known for highly specific catalysis. The shape and reactivity of a given enzyme limit its catalytic activity to a very small number of possible substrates. Enzymes are also known for speed, working at rates as high as 10,000 conversions per second per enzyme molecule. Enzyme biosensors rely on the specific chemical changes related to the enzyme/analyte interaction as the means for determining the presence of the targeted analyte. For example, upon interaction with an analyte, an enzyme may generate electrons, a colored chromophore or a chance in pH (due to release of protons) as the result of the relevant catalytic enzymatic reaction. Alternatively, upon interaction with an analyte, an enzyme may cause a change in a fluorescent or chemiluminescent signal that can be recorded by an appropriate detection system.

Immunosensors utilize antibodies as binding agents. Antibodies are protein molecules that bind with specific foreign entities, called antigens, that can be associated with disease states. Antibodies attach to antigens and either remove the antigens from a host and/or trigger an immune response. Antibodies are quite specific in their interactions and, unlike enzymes, they are capable of recognizing and selectively binding to very large bodies such as single cells. Thus, antibody-based biosensors allow for the identification of certain pathogens such as dangerous bacterial strains. As antibodies generally do not perform catalytic reactions, there is a need for special methods to record the moment of interaction between target analyte and recognition agent antibody. Changes in mass (surface plasmon resonance, acoustic sensing) are often recorded; other systems rely on fluorescent probes that give signals responsive to interaction between antibody and antigen. Alternatively, an enzyme bound to an antibody can be used to deliver the signal through the generation of color or electrons; the ELISA (Enzyme-Linked ImmunoSorbent Assay) is based on such a methodology.

DNA biosensors utilize the complimentary nature of the nucleic acid double-strands and are designed for the detection of DNA or RNA sequences usually associated with certain bacteria, viruses or given medical conditions. A sensor generally uses single-strands from a DNA double helix as the binding agent. The nucleic acid material in a given test sample is then denatured and placed into contact with the binding agent. If the strands in the test sample are complementary to the strands used as binding agent, the two interact. The interaction can be monitored by various means such as a change in mass at the sensor surface or the presence of a fluorescent or radioactive signal. Alternative arrangements have binding of the sample of interest to the sensor and subsequent treatment with labeled nucleic acid probes to allow for identification of the sequence(s) of interest.

Chemical sensors make use of non-biological macromolecules as binding agents. The binding agents show specificity to targeted analytes by virtue of the appropriate chemical functionalities in the macromolecules themselves. Typical applications include gas or heavy metal detection; the binding of analyte may change the conductivity of the sensor surface or lead to changes in charge that can be recorded by an appropriate field-effect transistor (FET). Several synthetic macromolecules have been used successfully for the selective chelation of heavy metals such as lead.

The present invention has applicability to all of the above noted binding agent classes.

Known methods of detecting interaction of analyte and binding agent can be grouped into several general categories: chemical, optical, acoustical, and electrical. In the last, an a voltage or current is applied to the sensor surface or an associated medium. As binding events occur on the sensor surface, there are changes in electrical properties of the system. The leaving signal is altered as function of analyte presence.

The most relevant prior art to the present invention involves sensors that are based on electrical means for analyte detection. There are several classes of sensors that make use of applied electrical signals for determination of analyte presence. "Amperometric" sensors make use of oxidation-reduction chemistries in which electrons or electrochemically active species are generated or transferred due to analyte presence. An enzyme that interacts with an analyte may produce electrons that are delivered to an appropriate electrode; alternately an amperometric sensor may employ two or more enzyme species, one interacting with analyte, while the other actually generates electrons as a function of the action of the first enzyme (a "coupled" enzyme system). Glucose oxidase has been used frequently in amperometric biosensors for glucose quantification for diabetics. Other amperometric sensors make use of electrochemically active species whose presence alter the system applied voltage as recorded at a given sensor electrode. Not all sensing systems can be adapted for electron generation or transfer, and thus many sensing needs cannot be met by amperometric methods alone. The general amperometric method makes use of an applied voltage and effects of electrochemically active species on said voltage. An example of an amperometric sensor is described in U.S. Pat. No. 5,593,852, in which Heller and Pishko disclose a glucose sensor that relies on electron transfer effected by a redox enzyme and electrochemically-active enzyme cofactor species. The present invention does not require application of an external voltage, oxidation/reduction chemistry, or electron generation/transfer.

An additional class of electrical sensing systems includes those sensors that make use primarily of changes in an electrical response of the sensor as a function of analyte presence. Some systems pass an electric current through a given medium; if analyte is present, there is a corresponding change in exit electrical signal, and this change implies that analyte is present. In some cases, the binding agent-analyte complex causes an altered signal, while in other systems, the bound analyte itself is the source of changed electrical response. Such sensors are distinguished from amperometric devices in that they do not necessarily require the transfer of electrons to an active electrode. Sensors based on the application of an electrical signal are not universal, in that they depend on alteration of voltage or current as a function of analyte presence; not all sensing systems can meet such a requirement. An example of this class of sensors is U.S. Pat. No. 5,698,089, in which Lewis and Freund disclose a chemical sensor in which analyte detection is determined by charge of an applied electrical signal. Binding of analyte to chemical moieties arranged in an array alters the conductivity of the array points; unique analytes can be determined by the overall changes in conductivity of all of the array points. The present invention does not rely on arrays or changes of applied electrical signal as a function of analyte presence. The present sensor does not make use of any applied electrical or electromagnetic signal.

Several other publications that do not fall into the preceding categories are worthy of mention in the prior art. Radmacher, et al. (*Science* 265:1577–1579 (1994)) noted the existence of augmented spatial fluctuations in enzymes interacting with substrates, but did not apply this phenomenon to analyte detection. Holzrichter, et al., U.S. Pat. No. 5,620,854, did make use of macromolecule motion to detect analyte; their system relies specifically on atomic force or scanning tunneling microscopes for detection of said motion. An additional patent is that of Stanbro, et al., U.S. Pat. No. 5,114,674, which discloses a sensor that is based on the interference of applied electrical fields. Interaction of target analyte with a binding agent alters the interference of the applied electrical field. The present invention does not make use of applied electrical fields, currents, or voltages.

Other prior-art voltage-based sensors require the use of semiconducting field-effect transistors (FET's) and rely on the chemical generation or physical trapping of charged species near the sensor surface. The method has found widespread use in the detection of positively-charged heavy metals as well as analytes that are involved in proton ($H^+$) generating enzyme reactions. Sato, et al. ("Endoscopic Urease Sensor System for Detecting *Helicobacter pylori* on Gastric Mucosa", *Gastrointestinal Endoscopy* 49: 32–38 (1999)) describe a pH-sensitive FET for the detection of the enzyme urease associated with the pathogenic bacteria *H. pylori*. The present invention does not rely on the use of a FET in the sensor element contacted to analyte-containing samples.

While hundreds of sensors have been described in patents and in the scientific literature, actual commercial use of such sensors remain limited. In particular, virtually all sensor designs set forth in the prior art contain one or more inherent weaknesses. Some lack the sensitivity and/or speed of detection necessary to accomplish certain tasks. Other sensors lack long-term stability. Still others cannot be sufficiently miniaturized to be commercially viable or are prohibitively expensive to produce. Some sensors must be pre-treated with salts and/or enzyme cofactors, a practice that is inefficient and bothersome. To date, virtually all sensors are limited by the known methods of determining that contact has occurred between an immobilized binding agent and targeted analytes. Use of fluorescent or other external detection probes adds to sensor production requirements and reduces lifetimes of such sensor systems. Additionally, the inventor believes that there is no sensor method disclosed in the prior art that is generally applicable to the vast majority of macromolecular binding agents, including enzymes, antibodies, antigens, nucleic acids, receptors, and synthetic binding agents.

It is therefore a primary object of the present invention to provide an improved sensor, utilizing a new method of detection, in which the fluctuations of macromolecular-associated electrostatic fields in proximity to an electrically-conducting base member induce de novo electron motion in the base member.

It is a further object of the invention to provide an improved sensor that rapidly detects analytes, and can be operated in a closed system that may contain dangerous samples.

It is yet another object of the invention to provide an improved sensor operating on a principle of electromagnetic induction, which is versatile in application, simple to use, inexpensive to produce, and demonstrates the sensitivity and long-term stability necessary for commercial application.

These and other objects of the present invention are attained by a sensor which has an electrically conductive or semiconductisve base member, and at least one macromolecular entity disposed proximate the base member and interactive at a level of specificity wit at least one predetermined analyte. An electrical signal is induced in the base member responsive to the interaction of the macromolecular entity with the analyte. A detection unit detects the induced electrical signal.

Optionally a self-assembled monolayer is bound to the base member, proximate the macromolecular entity. Macromolecular entities are arranged in a monolayer or multilayer.

According to an aspect of the invention a plurality of macromolecular entities is employed for the detection of at least one analyte.

According to another aspect of the invention electrical leads of the detection unit are coupled to the base member at no more than two positions of the base member. The coupling may be passive. The electrical connections may be coupled to a load for delivery of power thereto.

According to yet another aspect of the invention the base member is a conducting foil, coating, thin-film, ink, or solid piece.

According to still another aspect of the invention a plurality of base members is employed in detection of at least one analyte.

In a further aspect of the invention a packaging layer is disposed above the macromolecular entity, the packaging layer being soluble in a medium that contains the analyte.

The invention provides a method for detecting an analyte, having the following steps: providing an electrically conductive base member; immobilizing at least one macromolecule in proximity to the base member, wherein the macromolecule is capable of interacting at a level of specificity with a predetermined analyte; exposing analyte to the macromolecule; and detecting an electrical signal induced in or about the base member, wherein the detected electrical signal is responsive to analyte presence or interaction with the macromolecule. Optionally a self-assembled monolayer is bound to the base member, the macromolecules are immobilized proximate to the self-assembled monolayer.

According to another aspect of the invention, a plurality of macromolecules having different specificity of interaction are immobilized for the detection of at least one analyte.

Preferably the step of detecting is performed by coupling electrical leads of a detection unit to the base member at no more than two positions of the base member. The coupling may be passive.

According to still another aspect of the invention, a plurality of base members is provided in the detection of at least one analyte.

According to yet another aspect of the invention, the macromolecular entities are arranged in a monolayer or multilayer proximate the base member.

According to still another aspect of the invention, a packaging layer is disposed above the macromolecules, the packaging layer being soluble in a medium that contains the analyte.

According to an additional aspect of the invention, a further step comprises coupling the electrical connections to a load for delivery of power thereto.

For a better understanding of these and other objectives of the present invention, reference is made to the following detailed description of the invention, by way of example, which is to be read in conjunction with the following drawings, wherein.

Figure 1:
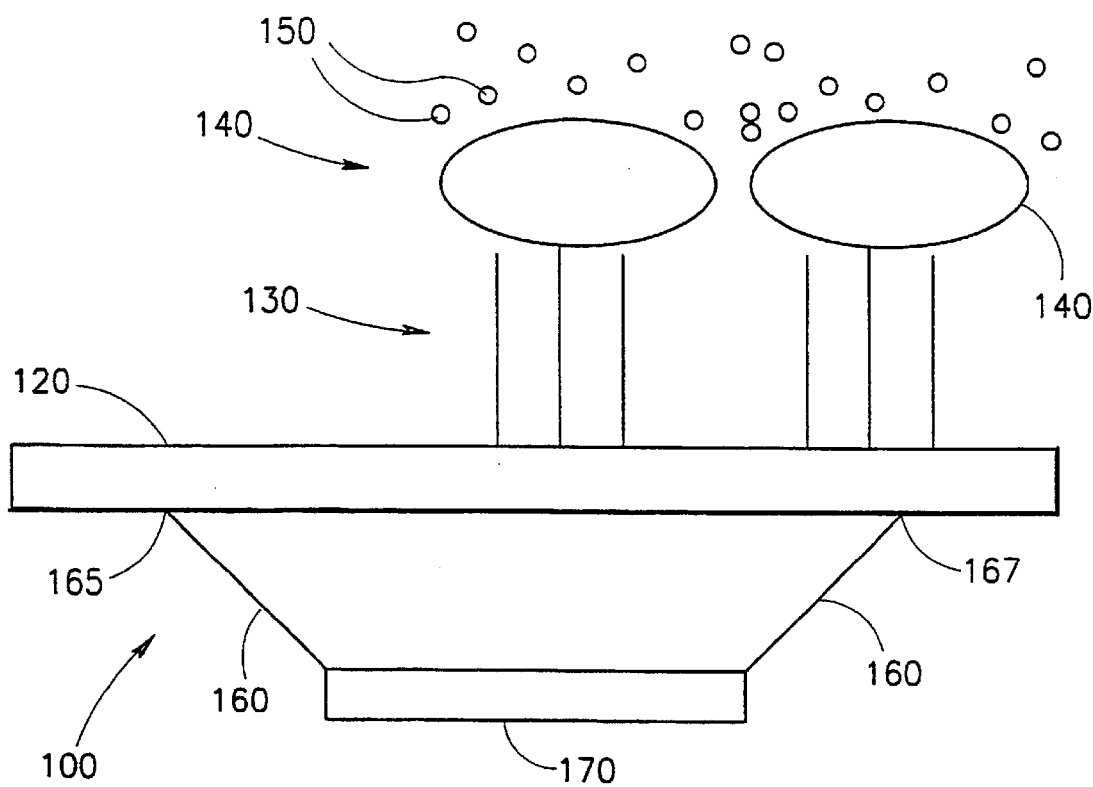
FIG. 1 is a schematic view of an embodiment of a sensor (100) in accordance with the invention, wherein macromolecular entities (140) are immobilized above a self assembled monolayer (130) and covered by a packaging layer (150), and having a base member (120) that is a solid conductive piece.

Without being bound by any particular theory, the following discussion is offered to facilitate understanding of the invention. The sensor design disclosed herein is based on electromagnetic induction of electrons in conducting materials when said electrons are exposed to fluctuating macromolecular electrostatic fields. The sensor utilizes a novel method of detecting an analyte wherein macromolecular binding agents are first immobilized proximate an electrically conductive base member. The bound macromolecules are always moving, the motion of the electrostatic fields associated with the macromolecules serve to generate an induced electrical signal in the base member. The fluctuating electrostatic fields generate fluctuating magnetic fields, and these fluctuating magnetic fields induce electron motion in the base member. Electrical signals such as induced current, induced electromotive force, changes in base member impedance or resistance, signal sign switching, signal frequency, electrical noise and components thereof can be monitored for change during exposure of the macromolecular binding agents to a sample that may contain target analyte. Changes in the electrostatic fields of the macromolecules before and during interaction with analyte result from altered motional behavior of the macromolecules themselves and/or the presence of additional electrostatic material associated with the analyte. Altered electrostatic fields (size) or changed macromolecule motions (rate of fluctuation) induce an altered electrical signal that can be easily recorded with an appropriate detection unit. In the embodiment shown in FIG. 7, changes in induced current as recorded across a resistor (775) by a voltmeter-based detection unit (770) is indicative of the presence of analyte in a sample exposed to a base-member (720) proximate a binding agent (740) that interacts at a level of specificity for the target analyte.

A typical sensor comprises (i) a multilayer substrate comprising a conducting base member or layer and an optional self-assembled monolayer (or other chemical entity that rests between the base member and the macromolecules); (ii) at least one macromolecule that displays a level of affinity of interaction toward a predetermined analyte or group of analytes; and (iii) a detection unit for measuring an electromotive force (emf), current or other electrical feature electromagnetically induced in or about the base member and responsive to the presence of analyte.

The sensor exploits the phenomenon of electromagnetic induction, the process by which fluctuating magnetic fields can induce electron motion in nearby electrically conducting materials. Since the sensor works on physical properties shared by nearly all macromolecular binding agents, the methodology is equally appropriate for a large variety of analyte classes, utilizing various macromolecular binding agents such as nucleic acids, enzymes, antibodies, antigens, peptides, or receptors. Additionally, charged or polar synthetic binding agents are appropriate for use in the present invention. The one requirement for binding agent is that it demonstrates a level of specificity of interaction with a predetermined analyte or group of analytes. The physical motion of macromolecules (proteins and DNA) immobilized in proximity to solid supports is of importance to the present sensor methodology and has been described in the scientific literature (Proteins on insulating mica: Thomson, N H, et al. *Biophysics Journal* 70:2421–2431 (1996); DNA on insulating mica: Bezanilla, M, et al *Biophysics Journal* 67: 2454–2459 (1994)).

According to a method of the invention, one first immobilizes one or more biological or synthetic macromolecules in proximity to an appropriately conductive base member and then measures an emf, current, or other electrical effect induced in said base member as a result of analyte-related changes in fluctuating electrostatic fields associated with the macromolecular binding agents. A change in motional behavior of the binding agent or addition of electrostatic material associated with the analyte causes an increased electromagnetic induction in the base member and thus signals binding of analyte. The amount of change in induced emf above background readings (generated by the immobilized macromolecules in motion) may be correlated to the concentration of analyte present in the sample of interest. Experience of the inventor has shown that non-specific interactions of sensor and sample do not produce a significant induced signal. Such conclusions are based on studies in complex matrices such as blood plasma, milk, stool, and ground beef homogenized in phosphate buffer.

The present sensor method has been successfully employed in numerous sensor systems (see Examples) and opens the door to the fast, sensitive, and inexpensive detection of a wide range analytes. A sensor as described in the present application has excellent sensitivity in detection (parts-per-billion or better) and, in short, has the properties and production features necessary for use in numerous domestic, law-enforcement, medical, pharmaceutical, food, hygiene and industrial applications.

The present invention is distinguished from the prior art in several ways. Firstly, the methodology is applicable to nearly all binding agents and not simply to those that produce or interact with electrons or electrochemically active compounds. Secondly, the method requires neither passage of electrical signal into a system nor detection of an electrical signal from a component of the material in contact with the binding agents. There is no requirement in the present invention for application of electromagnetic radiation, voltage, or electrical current. Additionally, the present invention does not require use of sample-contacting transistor devices or any active electrode species. It should be noted that the medium containing the analyte need not be electrically conductive, nor is the base member required to have a redox potential different from that of the analyte.

In the following description, numerous specific details are set forth in order to provide a thorough understanding of the present invention. It will be apparent, however, to one skilled in the art that the present invention may be practiced without these specific details. In other instances well known circuits and control logic have not been shown in detail in order not to unnecessarily obscure the present invention.

Certain terms are now defined in order to facilitate better understanding of the present invention. An "analyte" is a material that is the subject of detection or quantification. A "base member" or base layer is a solid or liquid element on or near which macromolecules can be physically or chemically immobilized for the purpose of sensor construction.

"Macromolecules", "macromolecular binding agents", or "macromolecular entities" can be any natural, mutated, synthetic, or semi-synthetic molecules that are capable of interacting with a predetermined analyte or group of analytes at a level of specificity.

A "self-assembled monolayer" (SAM) is herein defined as a class of chemicals that bind or interact spontaneously or otherwise with a metal, metal oxide, glass, quartz or modified polymer surface in order to form a chemisorbed monolayer. As the phrase "self-assembled" implies, a self-assembled monolayer is formed from molecules that bond with the surface upon their direct contact from solvent, vapor, or spray. As the word "monolayer" implies, a self-assembled monolayer possesses a molecular thickness, i.e., it is ideally no thicker than the length of the longest molecule used therein. In practice, this may not be the case, but a thicker chemical layer between macromolecules and base member is acceptable for sensor construction.

An "electrode" or "lead" is a wire, electrical lead, connection, or the like that is attached at one end to a detection unit and contacted at the other end directly or indirectly to a "sensor strip" of base member and associated macromolecules. Contact is generally electrically passive in nature and occurs at two positions.

"Induced" and "induction" have their normal meaning in the electrical arts with respect to electromagnetism. Specifically by these terms it is intended to exclude oxidation-reduction chemistries and applied electrical signals.

The sensor according to the invention exploits the fact that macromolecular binding agents and most relevant analytes are electrically-polar species. Such polarity is due to full charges, fixed dipoles, and induced dipoles. Proteins (enzymes, antibodies, receptors) and peptides are made up of amino acid building blocks, and several of the amino acid side chains are positively or negatively charged in solution. Lysine, arginine, and histidine can display net positive charge on their side chains, while aspartic acid and glutamic acid have negatively-charged side chains except at very low pH values. Nucleic acids have negatively charged phosphate groups, and polymers of nucleic acids are thus highly negatively-charged. Small metabolites and synthetic molecules are often charged or polar, while whole cells have exposed charges due to the presence of membrane proteins and phospholipids. When the present invention employs a binding agent that is not an enzyme, the macromolecular binding agent specifically sequesters a target analyte in proximity to the base member; the altered electrostatic fields associated with the binding agent-analyte complex increase induced electron motion in the base member relative to the situation prior to analyte presence. The signal that is induced in the base member is generally recorded within fifteen to thirty seconds. At very low analyte concentrations, there may be latency due to delays in analyte reaching the immobilized binding agent. Detection of *Salmonella ente-*

*riditis* at 10 cells per milliliter of ground beef-buffer solution required approximately 90 seconds. This high sensitivity may be related to the charges protein flagella on the bacteria; these flagella will continue to move—and thus add to the induced effects—when a bacterium is bound to an antibody binding agent proximate base member.

Figure 6:
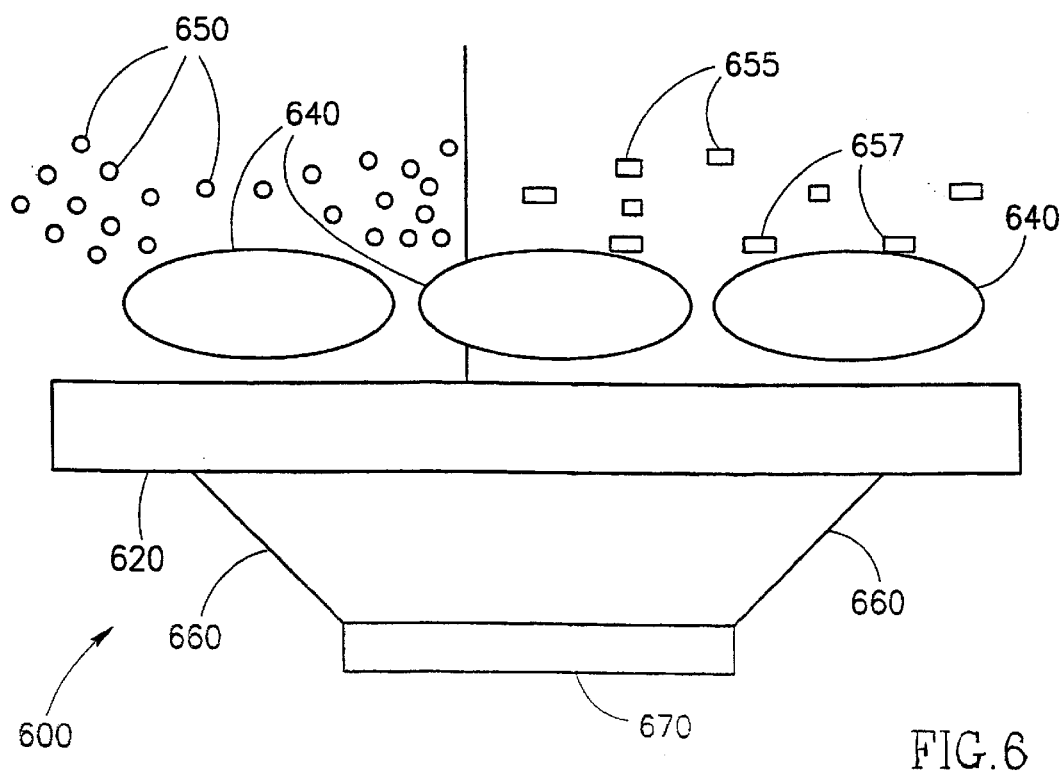
FIG. 6 is a schematic view of a fifth alternate embodiment of a sensor (600) in accordance with the invention which is similar to the embodiment of FIG. 4, in which a packaging layer (650) is present prior to analyte delivery (left side of figure) and absent (right side of figure) when analyte (655) is present and interacts (657) with the macromolecular binding agents (640)

Referring now to FIG. 6, which schematically illustrates a preferred embodiment of the invention, an analyte (655) is disposed proximate a sensor (600). The analyte (655) can be a member of any of the following categories, listed herein without limitation: cells, organic compounds, antibodies, antigens, virus particles, pathogenic bacteria, metals, metal complexes, ions, spores, yeasts, molds, cellular metabolites, enzyme inhibitors, receptor ligands, nerve agents, peptides, proteins, fatty acids, steroids, hormones, narcotic agents, synthetic molecules, medications, nucleic acid single-stranded or double-stranded polymers. The analyte (655) can be present in a solid, liquid, gas or aerosol. As will be seen below in the discussion of alternate embodiments, the analyte (655) could even be a group of different analytes, that is, a collection of distinct molecules, macromolecules, ions, organic compounds, viruses, spores, cells or the like that are the subject of detection or quantification. Some of the analyte (657) physically interacts with the sensor and causes an increase in electromagnetic induction in the conductive base member (620).

The sensor (100) as shown as a preferred embodiment in FIG. 1 includes a base member (120), which may be in the form of a solid piece, a chip, a foil, a wire, a coating, or a liquid. The base member (120) may be any conducting material such as metals, conducting organic polymers, conductive "inks", conductive liquids, or graphite. Low-resistivity semiconductor materials may also serve as the base member (120). Insulating and dielectric materials are not appropriate for the role of base member, although a base member may be coated onto an insulating material such as plastic. This is the situation in FIG. 5 in which a conducting coating, ink, or film (520) has been deposited on an electrically-insulating support (515). The insulating material (515) is then referred to as a "support" or "solid support" for the base member (520). Macroscopic properties of the base member include its electrically-conductive nature and possible reactivity with chemicals to form self-assembled monolayers. Microscopic properties of the base layer include free electrons that can move within the lattice of the atoms or ions that compose the base member. For use in the invention, a base member must show a level of electrical conductivity. Thus, a plastic container that is coated with a silver thin film has silver as the base, member on a plastic support. In this context, "conductive inks" coated or painted onto plastic disposable members are particularly useful as base members in the present invention. A conductive ink is defined as a liquid that contains, in part, electrically-conducting material. Organic volatiles evaporate over time and a conducting surface remains.

The preferred embodiments have the macromolecular binding agents immobilized proximate a conducting foil or deposited thin film base member. Preferred base member materials include but are not limited to aluminum, gold, silver, copper, conducting organic polymers, platinum, iridium palladium, rhodium, mercury, osmium, ruthenium, gallium arsenide, indium phosphide, mercury cadmium telluride, and the like. Aluminum foil and silver conductive inks are particularly preferred as they are conductive, inexpensive, food-safe, and amenable to treatment with self-assembled monolayers. Additionally, a natural oxide layer can provide electrical insulation between the conductive metal and the macromolecular electrostatic fields (to avoid short-out). Copper, gold, silver, and aluminum are particularly preferred as base member materials, especially foils or thin films of these metals on plastic supports. The macromolecules can be chemically or physically immobilized in proximity to the base member. The macromolecules can be immobilized directly to the base member or can interact with a chemical layer deposited on the base member.

Figure 2:
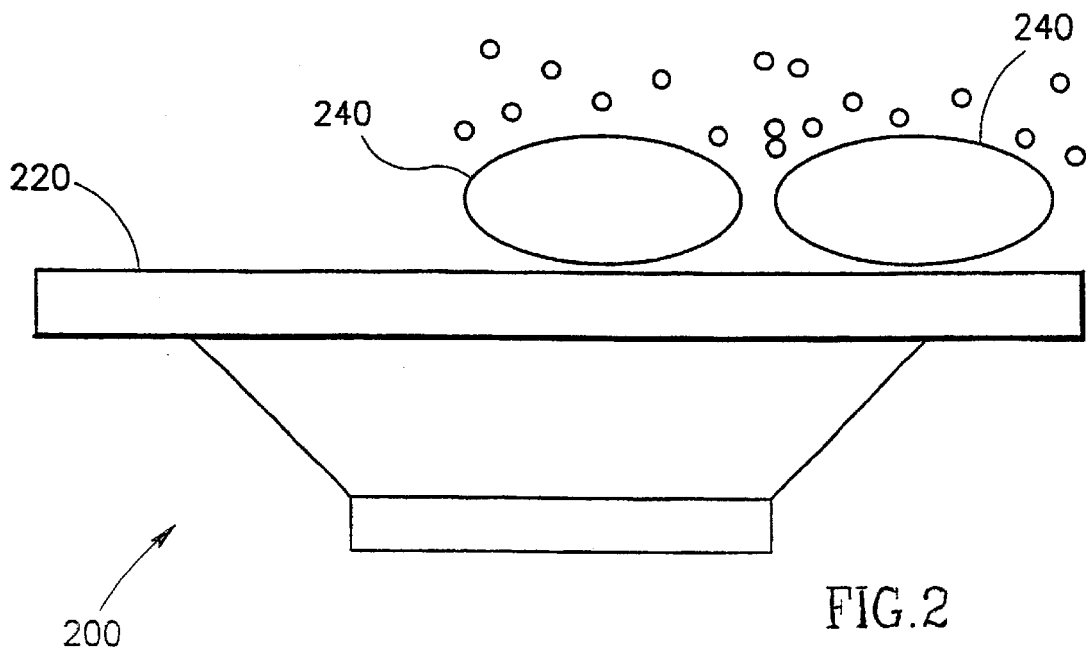
FIG. 2 is a schematic view of a first alternate embodiment of a sensor (200) in accordance with the invention which is similar to the embodiment shown in FIG. 1 except that the self assembled monolayer has been omitted and macromolecules (240) are physically absorbed proximate the base member (220)

Referring again to FIG. 6, a self-assembled monolayer (SAM) (630) is attached to the base member (620) by any appropriate method. The SAM ideally possesses molecular thickness, that is, that the entire chemical layer is only one molecule thick. The SAM (630) may serve to chemically or physically bind macromolecules (640), to aid in their long-term stabilization, to transduce signal resulting from interaction of macromolecules (640) with analyte (657) to the base member (620), or to provide differential levels of electrical connectivity between the macromolecules (640) and the base member (620). As shown in FIG. 2, and further disclosed below, macromolecules (240) may also be physically absorbed to the base member (220). If a SAM is applied, it may be a mixed SAM formed from several chemical components. Turning now to FIG. 1, chemicals (not shown) other than SAM's may be employed in certain applications, and serve the same role as defined for SAM's, namely binding, stabilization, or signal transduction. The SAM (630) generally forms on the base member by direct deposition from solution or through vapor deposition. SAM layers are generally formed from chemicals with formulae R—COOH, R—SH, R—S—S—R', R—S—R', R—SiCl$_3$, or R—Si—(OR")$_3$. R and R' are each composed of at least one organic functionality, while R" is either a methyl or ethyl group. The specific SAM (630) selected is a function of the base member material (620) employed.

The SAM (630) usually has surfactant properties. SAM's are formed from chemicals with generally formula R—COOH when aluminum foil or silver oxide serves as base member (Ulman, A. *Chemical Reviews* 96: 1533–1554 (1996)), R—SH, R—S—S—R', or R—S—R' when gold or silver is the base member, and R—SiCl$_3$ or R—Si—(OR")$_3$ when conductive doped silicon is the base member. The R-group of the SAM (630) may be any organic group and might contain an aromatic moiety in order to aid in amplification of the signal from the fluctuating macromolecular electromagnetic fields to the base member. A mixed SAM in which two different chemicals are deposited on the base member (620) may be employed. One chemical may serve to bind the macromolecules to the base member, while the other might aid in the physical stabilization of the macromolecules during dry storage of sensor "strips".

For R—COOH, if R is an aliphatic group, then the SAM is termed a fatty acid. Fatty acids are particularly appealing as they can form good insulation between the macromolecules and conducting members and are available from natural sources such as vegetable oils. Fatty acids have been shown to form SAM's on aluminum and copper (oxide) samples. R can also be aromatic in nature, and a SAM with a phenyl moiety offers significant electrical connectivity between the fluctuating macromolecular electrostatic fields and the electromagnetically-inducible electrons of the base member (620). As one of the strengths of any sensor is its cost, a preferred embodiment of the present invention can be prepared on commercially available aluminum foil. Cost per complete sensor strip (materials only) is well under one cent. SAM's (630) do not interfere with the electrical connection between the base member (620) and electrical leads (660) of an appropriate detection unit (670).

On etched silicon, organic alcohols readily (R—OH) form self-assembled monolayers. Appropriate SAM's for gold and silver include a wealth of sulfur containing compounds. Notable among them are organic thiols, sulfides, and disulfides.

Organic thiols correspond to the general formula RSH where R represents an organic moiety. R can be aryl, alkyl, a combination of the two, long- or short-chain. Preferably the pendant functional group is chosen from those functional groups that are reactive with amino (—$NH_2$) or other reactive groups on proteins, DNA, or synthetic binding agents, or that can be adapted to be reactive with said groups. Alternatively, the pendant group may be selected to provide stability to the macromolecules (640) by serving as either a source of hydrophilic or hydrophobic stabilization. Functional pendant groups that are reactive with amino groups or that are easily adapted to be reactive with amino groups include carboxylic acids that can be converted to more reactive functionalities. Functional pendant groups that stabilize enzymes by providing a source of hydrophilic interaction include hydroxyl and carboxylic acid moieties. Hydrophobic stabilization can be provided by pendant methyl or other appropriate alkyl and aryl groups.

Organic sulfides correspond to the general formula RSR' where R and R' represent organic moieties. The nature of R and R' can be varied to balance insulation and electrical connectivity between the macromolecules and the conductive base member. Once again, the terminal functional groups can be chosen from those functional groups that are reactive with the amino (—$NH_2$) or other functional groups on binding agents, or that can be easily adapted to be reactive with said groups. Alternatively, they may be selected to provide stability to macromolecules by serving as a source of hydrophilic or hydrophobic stabilization.

Organic disulfides correspond to the general formula RS—SR' where R and R' have the meanings given above.

Examples of macromolecular entities suitable for use in the sensor (600) include but are not limited to enzymes that recognize substrates and inhibitors; antibodies that bind antigens, antigens that recognize target antibodies, receptors that bind ligands, ligands that bind receptors, nucleic acid single-strand polymers that can bind to form DNA-DNA, RNA-RNA, or DNA-RNA double strands, and synthetic molecules that interact with targeted analytes. The present invention can thus make use of enzymes, peptides, proteins, antibodies, antigens, catalytic antibodies, fatty acids, receptors, receptor ligands, nucleic acid strands, as well as synthetic macromolecules in the role of macromolecules (640). Natural, synthetic, semi-synthetic, over-expressed and genetically-altered macromolecules may be employed as binding agents. The macromolecules (640) may form monolayers as in FIG. 1, multilayers as in FIG. 4, or mixed layers of several distinct binding agents as in FIG. 3. A monolayer of mixed binding agents may also be employed (not shown).

The macromolecule component is neither limited in type or number. Enzymes, peptides, receptors, receptor ligands, antibodies, catalytic antibodies, antigens, cells, fatty acids, synthetic molecules, and nucleic acids are possible macromolecular binding agents in the present invention. The sensor method may be applied to nearly any macromolecule because it relies on the following properties shared by substantially all macromolecular binding agents:

(1) that the macromolecules chosen as binding agents are highly specific molecules designed to bind only with a selected analyte or group of analytes;

(2) that macromolecules have associated electrostatic fields due to charged and electrically-polar components of the macromolecules:

(3) that the electrostatic fields (92, 94 in FIG. 9) associated with the macromolecular binding agents fluctuate or change significantly in the presence of target analyte or analytes; such fluctuations can be caused by additional motions of the binding agent (enzymes) or by additional electrostatic material from the analyte that contributes to the electrostatic environment (non-enzyme binding agents); and (4) that the fluctuating electrostatic fields can induce an analyte-responsive electrical signal in a nearby conducting base member.

For example, an induced current may be measured in a closed electrical circuit that contains the base member. A background induced current is present in the circuit due to fluctuations of the macromolecular electrostatic fields. Presence of analyte causes an increased electromotive force in the base member and thus a larger induced current as measured by a detection device that is electrically contacted to the base member at two positions.

The broad and generally applicable nature of the present invention is preserved during binding of macromolecules (140) in proximity to the base member (120) because binding can be effected by either specific covalent attachment or general physical absorption. It is to be emphasized that the change in electrical effect in the base member that is associated with analyte presence does not rely on any specific enzyme chemistries, optical effects, fluorescence, chemiluminescence, oxidation/reduction phenomena or applied electrical signals. This feature distinguishes the present invention with all known prior art. Additionally, according to the operation of the invention current is actually generated, and the generated electricity may be of use in powering devices such as the sensor itself.

The macromolecules (140) preferably rest within a distance not much larger than 50 nanometers (nm) from the base member (120) so as to allow for easy measurement of the electrical effects induced by fluctuating macromolecular electrostatic fields. A larger separation between macromolecules and base member is also possible. In such a case, a conductor, dielectric, or insulator may be disposed between the base member and the macromolecules. For the purposes of this invention, "proximate" with respect to macromolecule disposition relative the base member refers to any distance that allows for macromolecule-related induction of an electrical signal in the base member, said induced electrical signal being responsive to the presence of analyte. Thus, a type of commercial aluminum foil that is factory-coated with mineral oil has also proven acceptable for use as base member.

Figure 7:
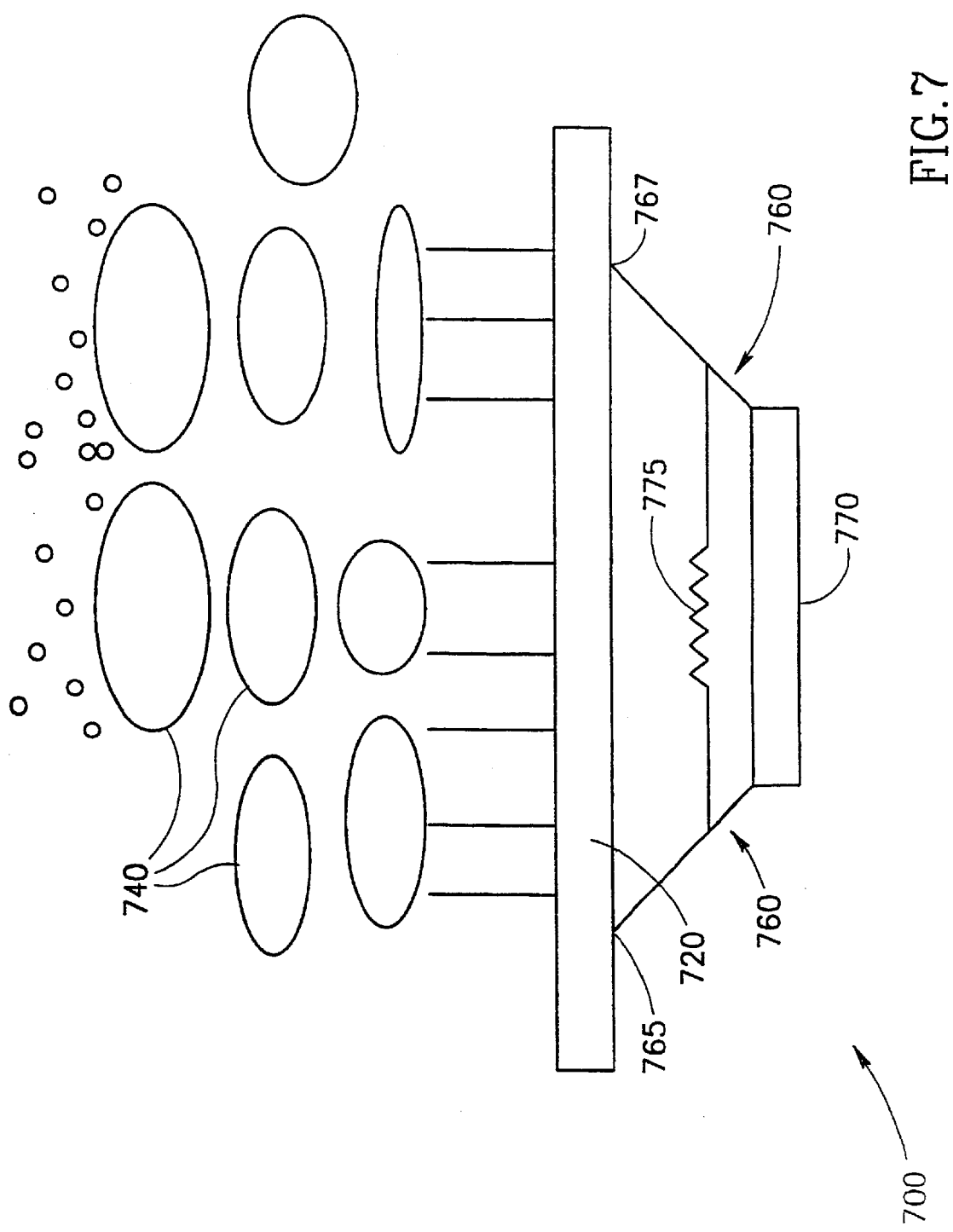
FIG. 7 is a schematic view of a sixth alternate embodiment of a sensor (700) in accordance with the invention in which induced current is measured or stored over a resistor (775) placed between electrodes (760) of a detection unit (770)

The detection unit (170) is any device that can detect one or more electrical signals induced in a conducting element as a function of analyte interaction with at least one macromolecular entity. Examples of such signals include but are not limited to induced current; induced electromotive force; voltage; impedance; signal sign, frequency component or noise signature of a predetermined electrical signal propagated into a base member at a first location and received at a second location. A voltmeter-based detection unit (770) as shown in FIG. 7 may have one or more additional resistors (775) built into its electronics so as to allow for measurement of the flow of electrons when the base member is part of an electrical circuit that includes the detection unit (770). While a detection unit may be based on a digital electrical metering device, it may also have additional functions that include but are not limited to data storage, data transfer, alert signaling, command/control functions, and process control. Detection units may be contacted through "leads" or "electrodes" (860–863) to one or more base members (820–823, FIG. 8). Referring again to FIG. 1, contacts between base member (120) and detection unit (170) are generally at two positions (165, 167) on the base member (120). As electrons build up at one end of the conductor, the other end becomes electron-deficient: an electromotive force develops in the conductor, and electrons can be made to flow in accordance with this electromotive force if the conductor is part of a closed electrical circuit. If the detection unit (570) is a voltmeter device with a very high internal impedance, one can measure the induced emf directly through passive contact of leads (560) to the base member (520). The size of the induced effect is proportional to the rate of fluctuation or size of the magnetic fields, while the direction of electron flow is such that it generates magnetic fields to opposes the causative fluctuating magnetic fields (Lenz's Law). If a detection unit contains an ammeter or voltmeter with an in-parallel resistor (775) (FIG. 7), the induced electromotive force can be measured as an induced current or voltage over the resistor (775).

The induced electrical signal is measured in the sensor strip in response to the continual motions of the charged macromolecules (140) prior to and during their interaction with analyte; changes in the measured electrical signal implies that analyte is present. Baseline readings are recorded for sample that lacks target analyte or analytes (FIGS. 10–13). Reference is now made to FIG. 6. Lower absolute induced electromotive force (induced emf) readings could theoretically result from reduced motion of macromolecules (640) in the presence of analyte (655, 657), while higher readings (in absolute terms) generally occur in response to greater enzyme motion or additional electrostatic material of the analyte (657) bound up with the macromolecules (640). Most sensor systems tested to date have shown increased electromotive force readings as a result of analyte (657) interaction with either enzymes, antibodies, protein (antibody or antigen) or nucleic acid single strands. "Increased" readings for the present invention can mean a more positive or a more negative signal value. In theory, there could be decreases in measured induced electrical effects due to analyte presence, but to date, only one system (monoclonal antibody for penicillin and penicillin) has shown such an effect. Digital voltmeters and ammeters are particularly preferred as components of the detection unit (670) for the present invention.

Figure 8:
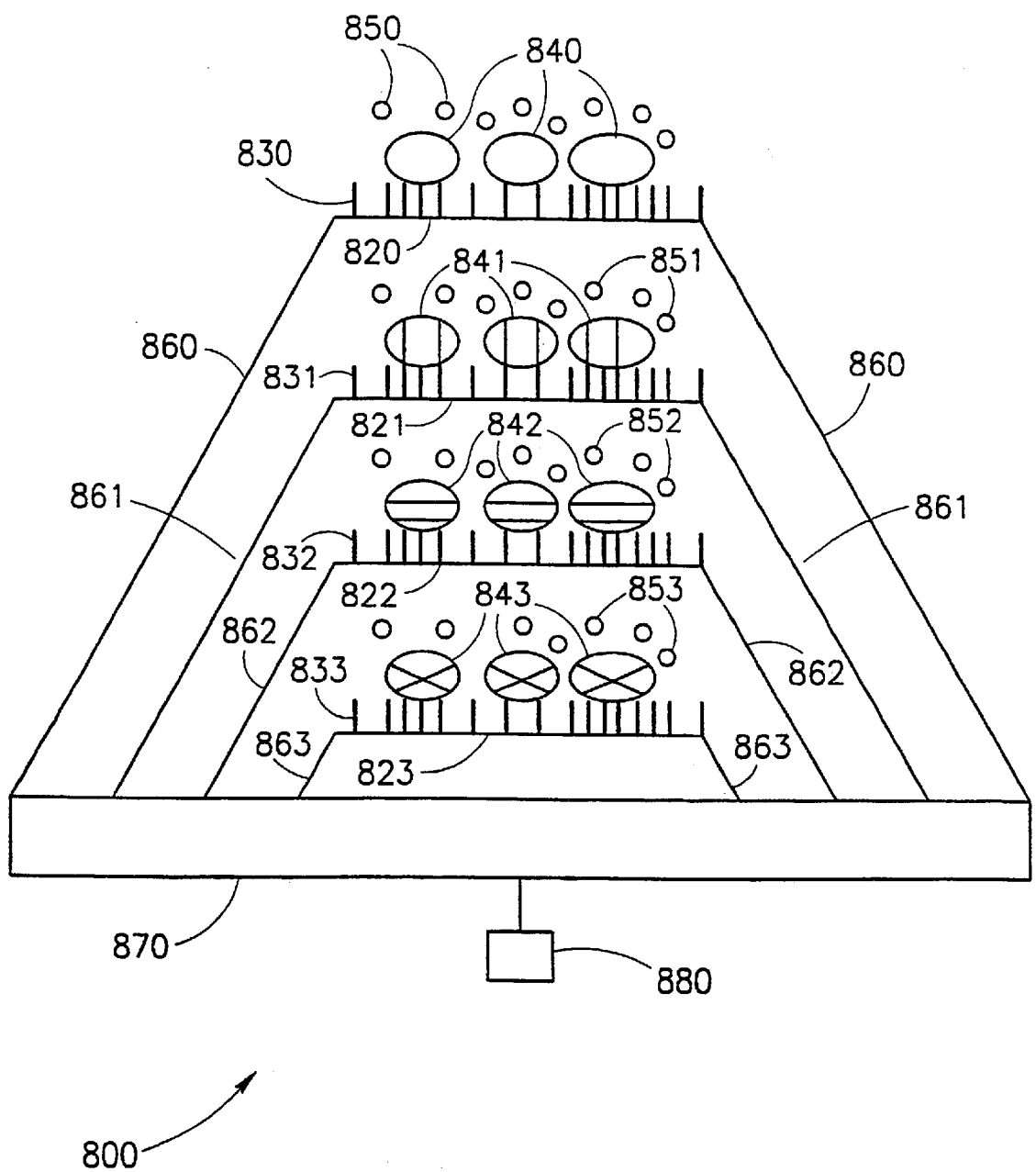
FIG. 8 is a schematic view of a seventh alternate embodiment of a sensor (800) in accordance with the invention in which a "multiplexed" plurality of base members (820–823) with different macromolecules (840–843) and optional SAM (830–833) and packaging (850–853) layers are employed and a computer control unit (880) monitors output from a detection unit (870)

The specific design of a detection unit depends on what quantity (current, frequency, impedance, etc.) is being observed. The detection unit may be integrated into a computer (880) as shown in FIG. 8 or other solid-state electronic device for easier signal processing and data storage. There are numerous arrangements of electrodes for measuring a emf, current, or other signal induced in the base member by the fluctuating macromolecular electrostatic fields. In the embodiment of FIG. 7, electrical leads (760) of a digital voltmeter-based detection unit (770) are contacted to a sensor strip base-member (720), at two points (765, 767) away from the region directly in contact with analyte (so as to keep all of the electrical connections dry and to protect the user). Induced electromotive force in the electrically conductive base member is recorded as a voltage differential across a resistor (775) attached to the leads, and the specific chance in voltage values prior to and during analyte exposure may be correlated to relative analyte concentration.

Referring again to FIG. 6, an optional packaging layer (650) for the sensor (600) is a layer of water-soluble chemicals deposited above the immobilized macromolecules (640). The packaging layer (650) is deposited by soaking or spraying methods. The packaging layer (650) serves to stabilize the macromolecules (640) during prolonged storage. In the absence of a packaging layer, oil and dirt may build up on the macromolecules (640) and may interfere with the rapid action of the sensor system. Glucose and a salt, such as NaCl, are typically used for the packaging layer (650) so as to guarantee their dissolution in aqueous samples, and thus facilitate interaction between macromolecular binding agent (640) and analytes (657). Other hydrophilic chemicals may be chosen. When the packaging layer dissolves (650), the binding agents are free to immediately interact with analyte (655, 657). Water-soluble polymers, sugars, salts, organic, and inorganic compounds are all appropriate for use in preparation of the packaging layer.

Figure 9:
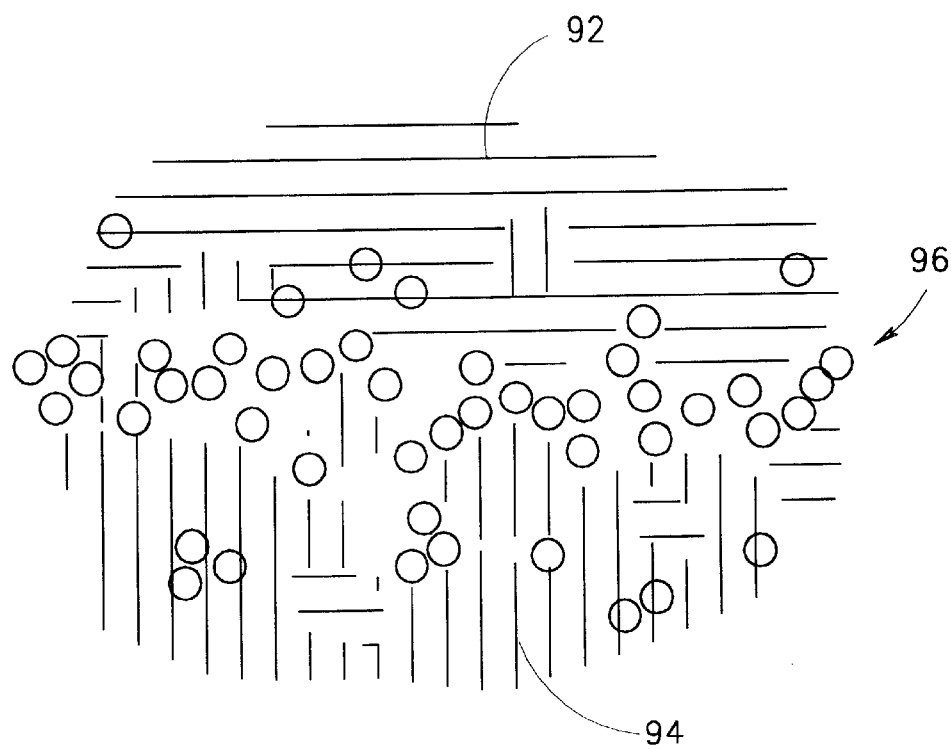
FIG. 9 is a schematic representation of a macromolecular species illustrating electrostatic fields (92, 94) associated therewith.

Referring to FIGS. 6 and 9, electrostatic fields (92, 94) associated with a macromolecular binding agent (corresponding to the macromolecules (640) in FIG. 6), fluctuate prior to and during interaction with analytes (657). The fluctuating fields (92, 94) increase in strength in the presence of analyte due to increased motion of the binding agent and/or increased electrostatic material contributed by the analyte (657). Fluctuating electrostatic fields give rise to fluctuating magnetic fields (not shown); these magnetic fields in turn induce motions of free electrons in a conductive base member (620). These electron motions induce an electrical signal in the base member. This induced electrical signal may be detected as an induced emf or current, impedance or resistance change, alteration in noise signature, sign change in a signal, alteration in electrical frequency or the like. Induced electrical signals are recorded through contact of appropriate electrical leads (660) of a detection unit (670). Referring to FIG. 1, contact between the leads (160) and the base member (120) usually occurs passively at two positions (165, 167). It will be appreciated by those skilled in the art that the electrical characteristics of the induced currents flowing within the base member (620) should vary when changes occur in the amplitude or frequency of motion of the electrostatic fields of the macromolecules (640).

The sensor makes use of fluctuations and changes in electrostatic fields (92, 94) associated with macromolecular binding agents. Such electrostatic fields are shown schematically as positive (field (92)) and negative (field (94)) regions in FIG. 9. Some of the atoms (96) of a hypothetical binding agent are shown. The electrostatic fields (represented as horizontal and vertical lines) are calculated according to the location of charged and polar moieties in the macromolecule. Real three-dimensional structures are generally determined from macromolecular x-ray crystallographic or nuclear magnetic resonance studies. The electrostatic fields (92, 94) of any particular macromolecule depend specifically on the spatial positions of charged/polar atoms or groups in the macromolecule. The atoms (96) in a macromolecule move when the macromolecule is tethered to a solid support; the associated electrostic fields (92,94) fluctuate with changing atomic positions. Analyte presence leads to either altered atomic motion of the macromolecule or additional electrostatic material contributed by the analyte.

In particular, when the binding agent, the macromolecules (640), is an enzyme, the presence of analyte (655) causes significantly increased lateral and horizontal motions of the charged enzyme macromolecules. The added motions of enzyme-associated electrostatic fields induce a greater electromotive force in the base member. Such analyte-related increases in enzyme motion have been previously described by Atomic Force Microscope studies (Radmacher, et al. i Science 265:1577–1579 (1994)). Thus, while there is a background induced electrical signal in the base member (620) as a result of the motion of free enzyme macromolecules (640) prior to their contact with analyte (657), introduction of analyte (655) results in significantly greater enzyme motions and resultant induced electromotive force. When the base member (620) has been part of a closed electrical circuit, induced current values of nearly 10 microamperes have been recorded.

Referring again to FIG. 7, in operation, the detection unit (770) may be calibrated for the lower background readings when target analyte or analytes are absent. In its prototypical embodiment, the sensor employs either a digital voltmeter or ammeter as part of the detection unit. If the detection unit (770) is a voltmeter-based device, an appropriate resistor (775) may be placed between the electrode leads (760); voltage readings are made across the resistor in a complete circuit that includes the resistor-containing electrodes (760), the detection unit (770) and the base member (720). An alternative ammeter-based detection unit (170) as shown in FIG. 1 is placed in series in a circuit that contains the base member (120), the leads (160) and the detection unit (170). A change in induced current as measured in a circuit that contains the base member (120) signals the presence of analyte, while the magnitude of the change may give information on analyte concentration. A detection unit may measure several different signals at once, such as induced current and signal frequency. The signal (induced emf, induced current, voltage, and the like) recorded by the detection unit generally fluctuates rapidly in value, as there is no coordination between the individual macromolecular entities. Thus, rapid changes in signal value or sign may serve to identify presence of analyte. A detection unit can be designed to produce an audible, visual, digital, or analog signal, alarm, or situation response due to analyte presence.

There are several points to note in regards to the method of detection of analyte as performed by the present invention Conducting materials are normally at a single electrical potential (voltage) at all points along their surfaces. In the present invention, variations in macromolecular electrostatic fields (92, 94) near a conductive base member (120) lead to the establishment of an induced emf in the base member (120). The induced emf results from electron motion in the base member in response to the fluctuating electrostatic fields of approximately $10^{12}$ macromolecules (140) per square centimeter of base member (120). The implications of the sensing methodology are significant. Firstly, sensing can take place far away from the point of macromolecule-analyte contact, as the effects of free electron motion are propagated throughout the electrically-conductive base member. This fact allows for closed-package "food sensing" or the sensing of potentially hazardous samples (blood) in closed containers. One portion of the sensor contacts the material of interest, while the leads (160) of a detection unit (170) are contacted to two positions (165, 167) elsewhere along the sensor strip. This is an important feature of the present sensor. The implications are that any material that can be recognized at a level of specificity by a peptide, protein, antibody, enzyme, nucleic acid single strand, or a synthetic binding agent can be detected safely in food, body fluids, air or other samples quickly, cheaply, and with high sensitivity. Response is very rapid. generally less than 30 seconds, cost is minimal, and experience of the inventor has shown that the sensors are very sensitive to dilute solutions of analyte (parts-per-billion or lower of antibiotics: 10 and fewer cells per milliliter of bacterial pathogens). Recent experiments by the inventor with an antibody-antigen system showed high induced current readings when the theoretical number of target analyte cells (*E. coli* 0157:H7) was one cell per milliliter of sample. Readings were forty-times those of background recorded in the absence of analyte.

Experience of the inventor has also shown that functioning macromolecules can induce easily measured voltages when an appropriate resistor (775) (FIG. 7) is placed in series with the base member (720), and the base member is part of a complete electrical circuit. The detection unit (770) makes use of the rule, V=IR, and the induced current is recorded as a voltage over a resistor (775) placed between the two electrodes (760). Typical current produced by a functioning sensor may be between 0.1 and 10 microamperes; these values can be converted to several hundred millivolts with an appropriate resistor. Recorded voltages for immobilized hen egg-white lysozyme (Sigma Chemicals) are typically 1 millivolt in air, 10 millivolts in water, and well over 200 millivolts when bacteria—the lysozyme substrate—are present. The specific signal values depend on the size of resistor placed between the leads and the voltmeter electronics. Though the voltage readings generally fluctuate, the range of values may be associated with the concentration of bacteria (analyte in this example) present in the sample at low concentrations of analyte. The measured current is generally in the microampere range, so kilo-ohm resistors allow for easy measurement of induced currents by commercial digital voltmeter modules. In the absence of binding agent (enzyme in this case) or in the presence of heat-inactivated enzyme, there is no recorded voltage. Macromolecular binding agents, SAM's and native oxide layers do not interfere with the direct electrical contacting of electrodes to the conducting base member.

A first alternate embodiment of the invention is shown in FIG. 2. This is similar to the first embodiment, except that the SAM has been omitted. This arrangement is useful in applications where low cost or quick production is a driving factor.

Figure 3:
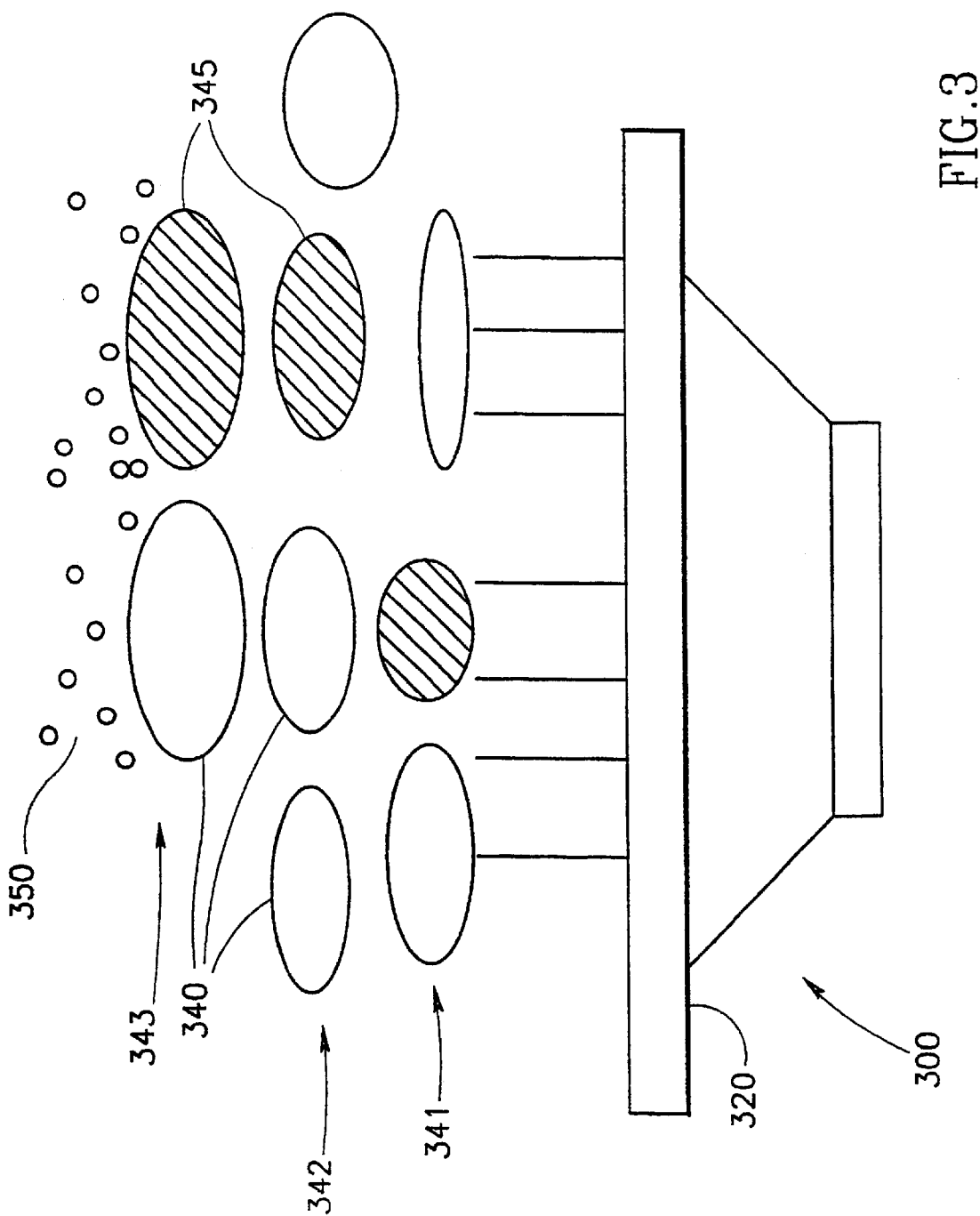
FIG. 3 is a schematic view of a second alternate embodiment of a sensor (300) which is similar to the embodiment shown in FIG. 2 except that macromolecules are immobilized as a multilayer (341, 342, 343) of two different macromolecular entities (340, 345)

A second alternate embodiment of the invention is shown in FIG. 3. wherein macromolecules of different specificities of interaction with at least one analyte (340, 345) are arranged in a plurality of layers (341, 342, 343). The macromolecules (340, 345) may be selected to bind with the same or different analytes. The different macromolecular binding agents are indicated by hatched ellipses (340) and un-hatched ellipses (345), respectively. This feature of multiple binding agents on a single base member (320) enables multiple binding opportunities for a single analyte or multi-targeting of a group of analytes. As discussed above in the first embodiment, the base member (320) may be a solid foil, or other suitable material as may be advantageous for a particular application.

Figure 4:
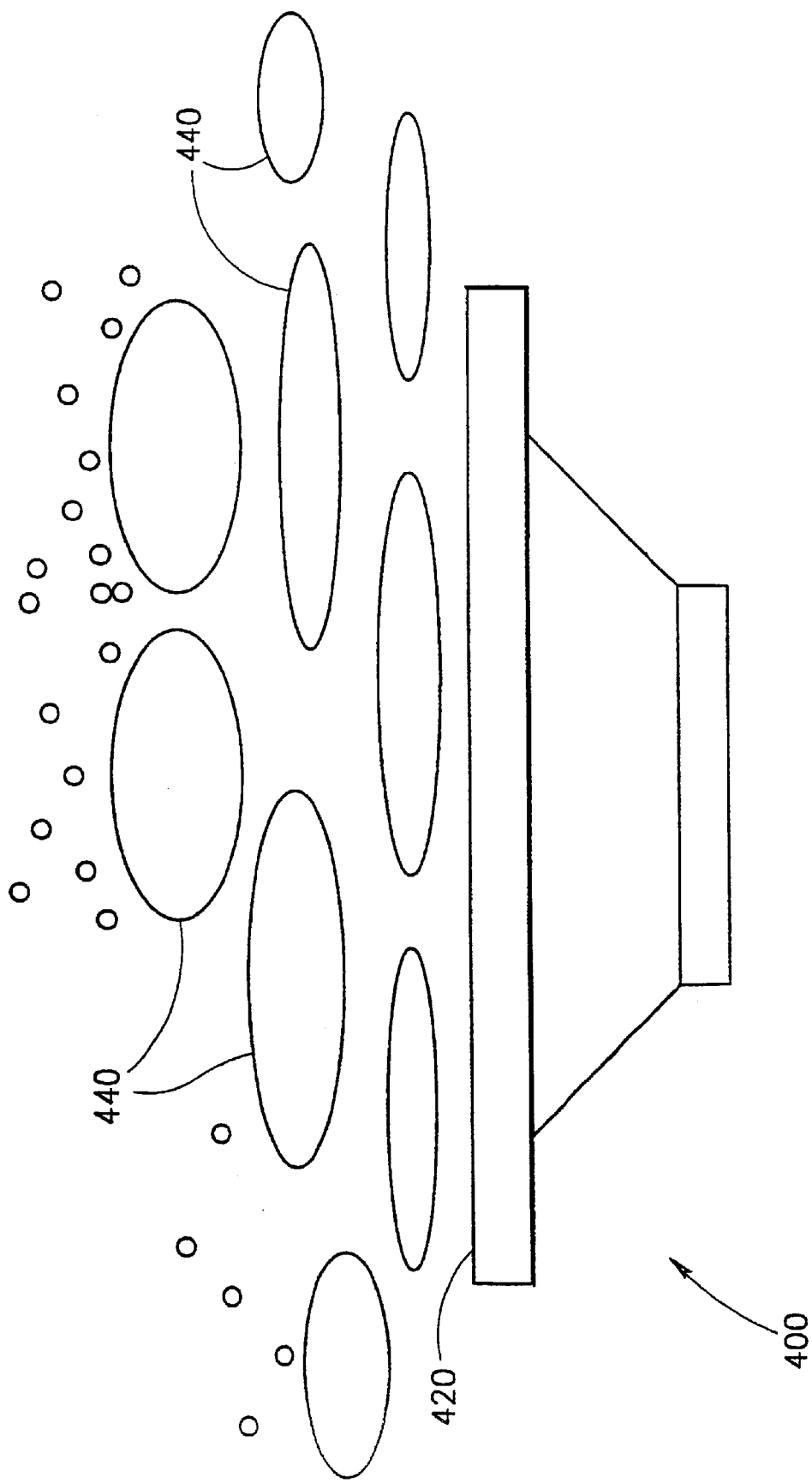
FIG. 4 is a schematic view of a third alternate embodiment of a sensor (400) which is similar to the embodiment shown in FIG. 3 except that one type of macromolecule (440) occupies the multilayer.

A third alternate embodiment of the invention is shown in FIG. 4, which is similar to the embodiment of FIG. 3, except that the macromolecule multilayer is composed entirely of one type of binding agent (440). As discussed above in the first embodiment, the base member (420) may be a solid foil, or other suitable material as may be advantageous for a particular application. The output of a sensor as in FIG. 7 (700) is optionally connected across a load resistance (775). The load resistance (775) may be applied as power in a device that requires electrical energy for operation.

Figure 5:
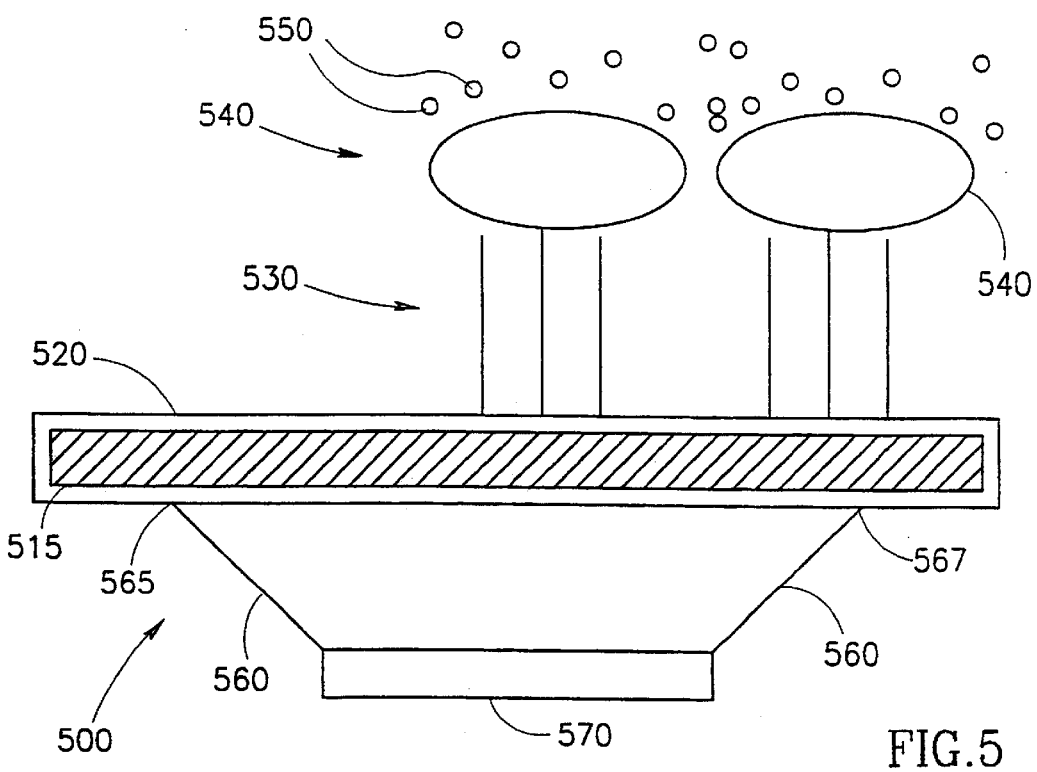
FIG. 5 is a schematic view of a fourth alternate embodiment of a sensor (500) in accordance with the invention wherein a base member (520) is a conductive coating, thin film or ink on a non-conducting solid support (515)

A fourth alternate embodiment, shown in FIG. 5, has a conductive ink, thin film, or coating serve as the base member (520). The conductive material (520) is deposited on a non-conductive support (515) such as the plastic of a disposable container or element. An optional SAM (530) may be deposited, and then macromolecules (540) and packaging layer (550) are deposited to yield a functional sensor strip that may then be contacted to the leads (560) of an appropriate detection unit (570). There must be electrical continuity between the portion of the base member (520) contacted to analyte-containing sample and the contact points (565, 567) of the electodes (560). The base member itself does not necessarily have to provide this continuity, although it may be deposited so as to allow for full electrical connectivity.

Referring now to FIG. 8, the device and methodology described here lend themselves to "multitasking" in which one or several analytes are detected by the use of one or several distinct binding agents (840–843) either on a single base member or on separate base members (820–823). In the latter case, base members are either monitored for induced emf simultaneously by a detection unit (870), or each base member is interrogated in a pre-determined order by the detection unit (870). Analyte presence is determined by the behavior of each sensor strip in the multiplexed unit. For example, a sensor (800) might be constructed from four separate base members (820–823). A carboxylic acid-based SAM (830–833), antibodies specific for different food pathogens (840–843), and a water-soluble "packaging layer" (850–853) are deposited separately on each base member. The distinct macromolecular entities are shown as clear ellipses (840), ellipses with vertical lines (841), horizontal lines (842), and crossed lines (843). A multiplexed detection unit (870) has two electrical leads (860-863) contacted to each base member, and a computer processor (880) monitors induced emf for all four sensor "strips" when a food sample is brought into contact with the sensor's multiplexed strips. Altered induced current (versus a predetermined background for each strip) associated with particular base members signals the presence of specific pathogens in the sample. The pathogens detected are directly correlated to the specific antibodies associated with each base member that displays an increased induced emf or current. For example, if the base member (823) that supports a particular antibody (843) shows a higher induced emf, then one may conclude that the pathogen target which the antibody (843) recognizes is present in the food sample. Multiplexing is not limited in number of base member or types of macromolecules simultaneously employed. Base member size can be micron-scale for large-scale sensing or detection operations. Screening of combinatorial libraries may require hundreds of separate base members with associated macromolecular entities for the detection of potential pharmaceutical lead compounds.

The sensor described in this application is very versatile in its preparation. A simple food sensor may have an enzyme or a group of antibodies (for *E. coli* 0157:H7, Listeria, Salmonella, Vibrio and other pathogens) absorbed to a piece of aluminum foil. A more complex medical sensor might require the use of a solid-state electronic device that converts the signal into an action such as release of a drug in response to changes in induced emf. Some semiconductors are of use in the present invention. An appropriate semiconductor has a low resistivity and is electrically responsive to fluctuating magnetic fields. While a single sensor strip may recognizes a particular analyte; multiplexed devices have multiple strips for detection of several target analytes or for redundancy to reduce false readings. Several different macromolecular binding agents may be immobilized in proximity to one or multiple base members in order to identify an analyte or a group of analytes. Thus, one might use four strips with different binding agents (two with unique antibodies, two with identical nucleic acid polymers) in order to definitively identify a single pathogen target with a low rate of false positive readings (the systems has redundancy built into it with the use of two strips with the same binding agent as well as different antibodies for the same pathogen target).

The present invention has several advantages:

First, the invention allows for the creation of very small sensors due to the ability to attach macromolecules in high concentration. The device, independent of electrical connections, has been made as small as millimeter dimensions and should be appropriate for IC fabrication in micron dimensions for the sensor strips of base member and associated macromolecules.

Second the sensor is inexpensive and quick to assemble. A fully functional sensor strip can be made in less than one-half an hour. All of the requisite materials are generally non-toxic, and the completed sensor strips can be sterilized.

Third, the sensor exhibits high detection selectivity. Enzymes are quiet specific for their substrates, antibodies are for antigens. Nucleic acid double-strand interactions can be quite specific as can be receptor-ligand interactions. Synthetic binding agents may also be used for specific detection of target analytes Thus, the sensor in different possible embodiments has high selectivity and sensitivity for the desired application. Parts-per-billion detection have been routinely performed with antibiotic-detecting sensors prepared with the enzyme penicillinase (see Examples below).

Fourth, the sensors exhibit long-term stability. In part, this fact is related to the simplicity of the design that significantly reduces the number of materials used in sensor strip preparation (base member, optional SAM layer, macromolecules, optional packaging layer). Primarily, this feature is due to the stability of the materials used to make the device. Immobilized macromolecules have been found at times to be more stable than their solution counterparts (for example, Dekker, R F, *Applied Biochemistry and Biotechnology* 22:289–310 (1989)), as the support material can offer protection from extreme environmental conditions. SAM's and packaging layers can also be selected to offer physical and chemical stabilization of bound macromolecules in order to further enhance their long-term stability.

Fifth, the sensor provides a near-instantaneous readout. Once enzymes begin to increase movements in the presence of analyte, there is a concomitant increase in electron induction in the base member; similarly, once analyte has bound to an immobilized binding agent, there is a change in the electrostatic potential near the base member and a corresponding increase in induced emf in the base member. This speed is a major benefit as most sensor systems in the prior art have time-delays of minutes to hours due to detection response. Speed is absolutely critical in such applications as poison gas detection or food pathogen identification. Altered macromolecular motions and changed electrostatic fields occur instantaneously with the arrival of analyte, and the response is generally recorded within 5 to 15 seconds—depending on the conductive properties of the base member. The sample can be delivered to the sensor via solid, liquid, gas, or aerosol media. Thus, one can expect to monitor for poison gas, food pathogens and blood antibodies and much more.

Sixth, the design is highly flexible. For instance, if one wishes to detect several analytes at once, appropriate macromolecules are selected and placed on separately-monitored strips of conductor base member in a multiplexed format. In addition, if one wishes to adjust the sensitivity of the device a number of means are available. For example, one can change the number, type or chemical composition of the macromolecule component through chemical or genetic manipulations. Alternatively, the length or nature of the organic groups in the SAM layer can be altered. In addition, the conductive member can be chosen from a variety of materials having different resistivities. Appropriate semiconductor materials may be used for further modulation of the signal strength relative to analyte concentration. The detection unit may also be modified by changing resistors (V=IR) used in induced emf detection. Finally, the orientation of the macromolecules on the device can be manipulated so as to allow for specific orientation of all macromolecules.

Seventh, the sensor is simple to use. One simply places the sample of interest in contact with a sensor strip and the detection unit determines target analyte presence as a function of the induced electrical effect measured between two locations of the base member. No additional components, such as supplemental reagents, are required.

Eighth, perhaps the greatest strength of this sensor design rests in the mode of detection. The vast majority of sensors rely on optical methods, applied electrical currents or specific detectable chemistries that are associated with enzyme catalysis for detection, such as a pH change, color generation or electron transfer (for example). This requirement significantly reduces the pool of macromolecules amenable to sensor usage in such devices: enzymes such as lysozyme that perform hydrolyses cannot easily be used in the current sensor architectures. The present sensor, in contrast, relies on electrostatic properties exhibited by all charged macromolecules. Thus, any macromolecule that can interact at a level of specificity with a given analyze or group of analytes should fin use in the present methodology. This development significantly increases the number of target analyte molecules that can be routinely detected. This is a major consideration in food safety sensing in which speed, cost, sensitivity, and flexibility of target selection are of primary importance.

Finally, the sensor strips actually produce energy. Typical sensor strips produce microampere quantities of current. Such electrical energy from a multiplexed system could be used to power the detector unit or find use in battery applications. Thousands of such strips lithographically produced on a chip could produce significant amounts of energy at low cost and in an environmentally-friendly manner.

The following table lists some of the possible components, inducible electrical signals and target application markets relevant to the present invention. Each grouping is independent of the others and one may combine a base member, a macromolecule, and an electrical signal for an application area of choice. The table is in no way meant to be limiting in scope or spirit of the present invention.

| Base Member | Macro-molecule | Electrical Signal | Application |
| --- | --- | --- | --- |
| Metal | Enzyme | Induced emf | Food Safety |
| Conductive Film* | Antibody | Induced Current | Chemicals |
| Organic Conductor | Nucleic Acids | Impedance | Biologicals |
| Conductive Liquid | | Resistance | Environment |
| Conductive Ink | Fatty Acid | Sign Switching | Industrial Hygiene |
| Graphite | Receptor | Frequency | Internet Medicine |
| Semiconductor | Synthetic-Protein | Noise Signature | Genetic Testing |
| | Peptide | Electromagnetic-Inductance | Diagnostics |
| | Cell | Capacitance | Process Control |
| | Catalytic-Antibody | | Drug Screening |
| | | | Drug Release |
| | | | Glucose Testing |

-continued

| Base Member | Macro-molecule | Electrical Signal | Application |
| --- | --- | --- | --- |
| | Synthetic Receptor | | Law Enforcement |
| | Receptor | | Veterinary-Testing |
| | Ligand | | |
| | Antigen | | |

*A conductive film can be deposited on a solid support by any means, including electroless deposition, spin coating, sputtering, vapor deposition, "printing" or dip-coating.

Figure 10:
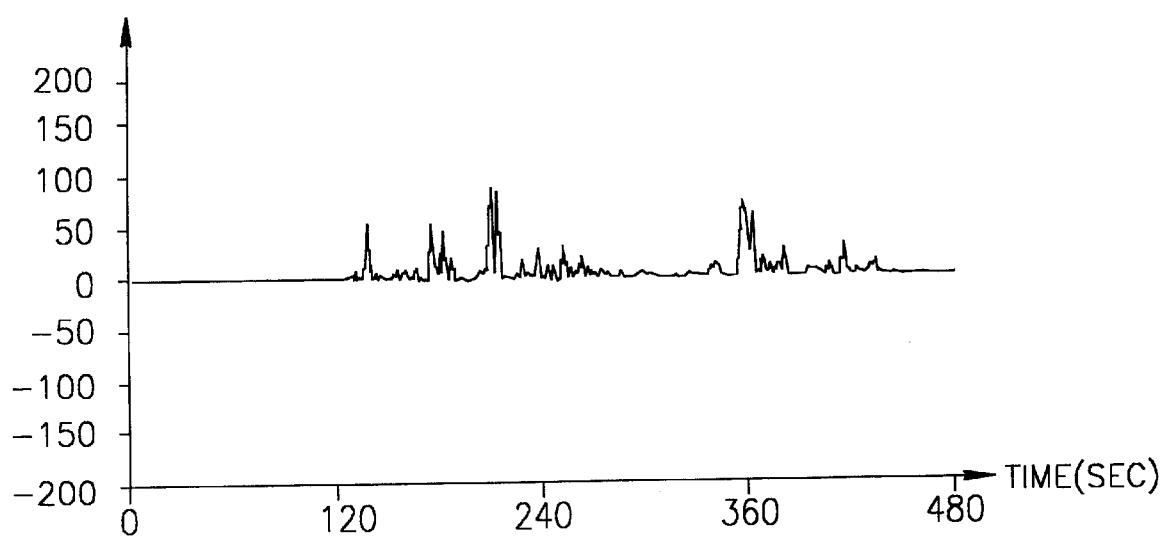
FIG. 10 is a plot of current induced in a base member (measured as voltage over a 150-kilo-ohm resistor) versus time for the reaction of the macromolecule lysozyme with its substrate, bacteria.
Figure 11:
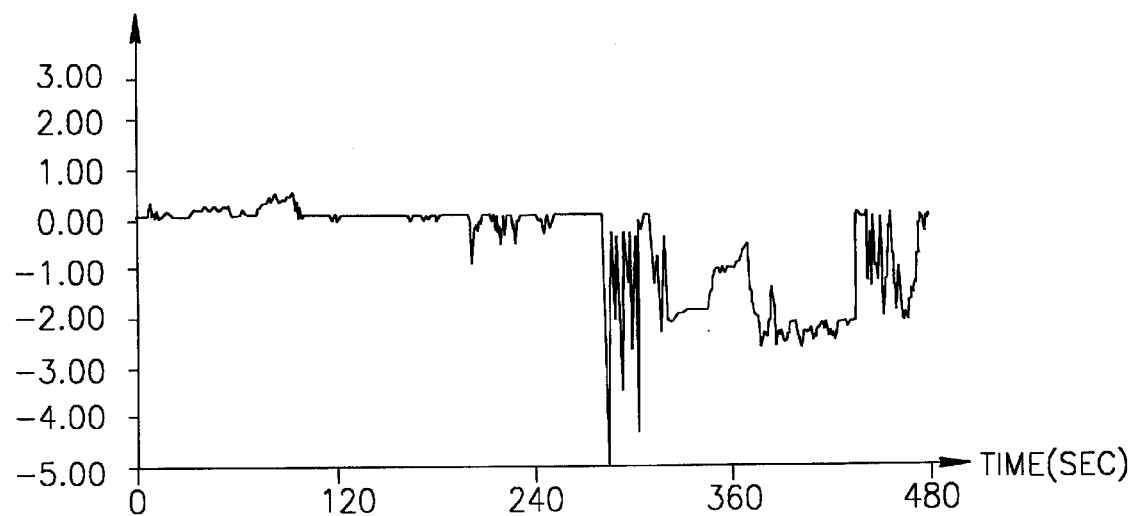
FIG. 11 is a plot of current induced in a base member versus time for the reaction of the macromolecule lysozyme with its substrate, bacteria.
Figure 12:
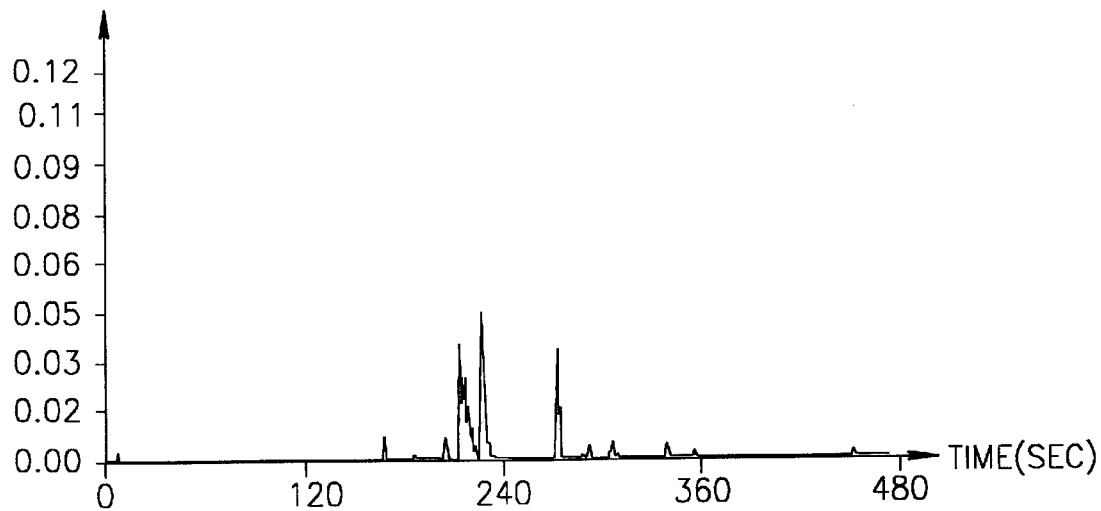
FIG. 12 is a plot of signal frequency versus time for the reaction of the macromolecule lysozyme with its substrate, bacteria.

FIGS. 10–13 show plots of sensing experiments performed with the present invention. In the experiments relevant to FIGS. 10–12, using the embodiment of FIG. 1, the enzyme lysozyme (Sigma Chemical Company, St. Louis, USA, catalogue number L-6876) was immobilized in proximity to a SAM (formed from an aqueous solution of parahydroxybenzoic acid, Aldrich Chemical Company, Milwaukee, USA, catalogue number H-5376) deposited on commercial aluminum foil (Reynolds Diamond Foil). A packaging layer of sodium chloride and glucose (Sigma, G-7528) was deposited above the enzyme layer. Sensor strips were cut from a larger sheet (approximately 10 cm×10 cm). In the experiments recorded in FIGS. 10 and 12, the sensor strips were partially inserted into a disposable plastic 1.5 milliliter tube; readings were made by contacting the leads of a commercially-available digital multimeter (Radio Shack, catalogue number 22-168A, supplied with PC port connection and data display software) to two points of the base member on the outside of the disposable tube. In the experiment shown in FIG. 11, a larger "strip" (approximately 3 cm×6 cm) was employed. Water, then bacteria, were placed on the strip, which was then folded over upon itself. Contact with water/bacteria occurred on the "inside", while contact with the same multimeter leads was performed on the dry, exposed "outside". In all measurements, background against boiled water was measured for approximately 90 seconds. The boiled water was assumed to be devoid of live bacteria. Bacteria (Sigma, M-3770) were added to the water and exposed to the sensing strip. This process required approximately thirty seconds, after which readings were resumed. FIG. 10 shows the induced current read as a voltage over a 150 kilo-ohm resistor that was connected to the multimeter leads. FIG. 11 shows the current induced in the base member-containing circuit, while FIG. 12 shows the electrical frequency recorded during lysozyme action. In all three systems, significant signals appear specifically when bacteria were present.

Figure 13:
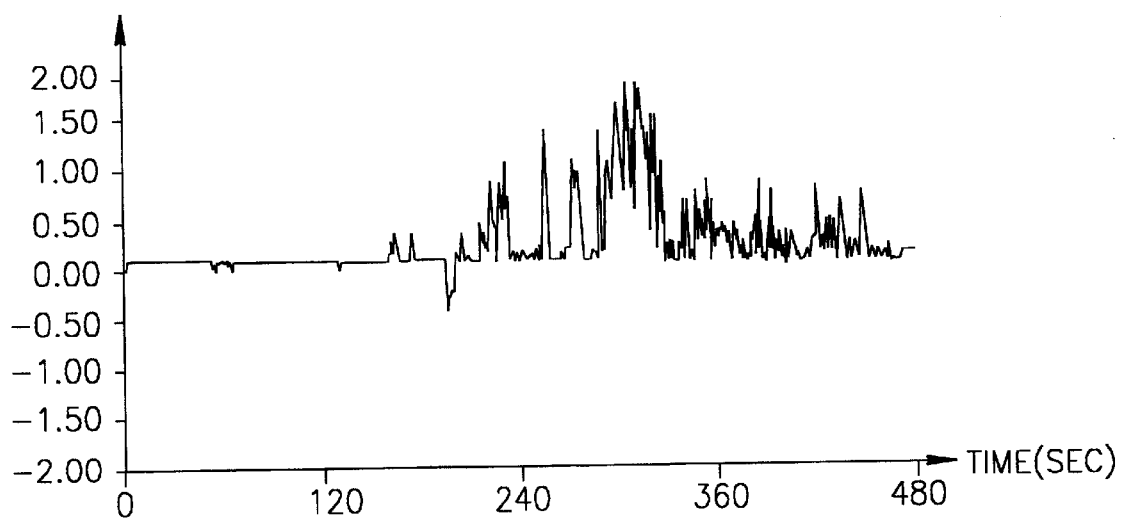
FIG. 13 is a plot of current induced in a base member versus time for the interaction of sodium chloride, then lithium chloride with the binding agent 12-crown-4.

FIG. 13 shows data for a chemical sensor, according to the embodiment of FIG. 2, except that the packaging layer was omitted. Crown ethers are known to coordinate metals. Specifically, 12-crown-4 coordinates lithium, but does not bind the larger sodium ion. 12-crown-4 (Aldrich, 19,490–5) was immobilized on aluminum foil from an aqueous solution of the crown either. The foil was next rinsed in water. Sensor strips were cut from the prepared sheets. The strips were placed in disposable tubes as described above for the lysozme system. For one minute, a background was recorded against water. During the next minute, the sensor strip was challenged with sodium chloride. Afterwards, lithium chloride (Aldrich, 31,046–8) was added. The plot shows induced emf in the base member (recorded as an induced current) during the experiment. Though the crown ether is a relatively rigid molecule, binding of positive lithium ions led to relatively large induced currents as measured between two points of the exposed sensor strip.

Figure 14:
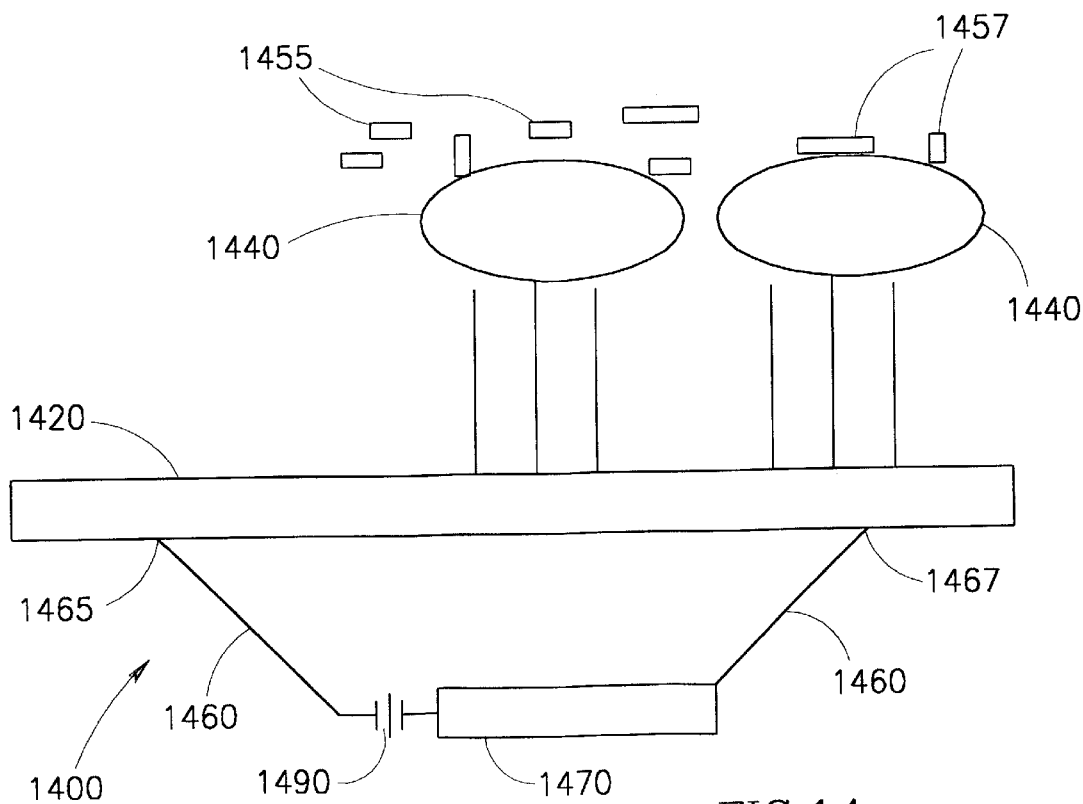
FIG. 14 is a schematic view of a seventh alternate embodiment of a sensor (1400) in which an optional source of an electrical signal (1490) is integrated into the sensor system.

There is one additional embodiment of the present invention that merits discussion. In this application, the sensor has been presented as a system that does not require the application of an external electrical signal. In the previously discussed embodiments, the electrical connections between the detection unit and the base member have been completely passive, that is to say, not requiring application of any external power, and utilizing no more than two points of connection. This presentation emphasizes a point of distinction between the present invention and prior art that makes use of applied signals and changes in exit signal as a function of analyte presence. One may however make an embodiment of the present invention that does make use of applied electrical signal; changes in the output signal are correlated to analyte presence. As shown in FIG. 14, the sensor (1400) is similar to other embodiments with the addition of a power source (1490) in the electrical circuit. Tne induced electromotive force in the base alters the exit signal and the size of change in signal is used to determine if analyte is present. The changes in applied signal result from electromagnetic induction in the base member (1420) and not from any electrochemical phenomena or specific electrical properties associated with either the analytes, medium, binding agents, or associated cofactors. If one measures resistance between two points (1465, 1467) of a base member (1420) with appropriate electrical leads (1460), the resistance fluctuates during sensor (1400) function. A power source (1490) applies a current through contact of an electrode (1460) to the base member (at position 1465), and the induced emf generated in the base member (1420) as a function of macromolecule (1440) interaction with target analyte (1457) causes fluctuations in the resistance reading that is calculated from voltage that reaches the contact point (1467) of the second electrode (1460) and then is measured by the detection unit (1470). This variation is correlated to changes in induced emf in the base member and its effect on the applied current that is used to measure resistance in the base member. The phenomenon may be due to the Hall effect, in which magnetic fields are applied to a current flowing in a conductor. In the present invention, the moving macromolecular entities (1440) act as the source of the magnetic fields. Experiments with applied power in the present invention have been successfully performed with the 12-crown-4/LiCl system previously described.

EXAMPLE 1

A piece of commercially-available aluminum foil (10 cm by 10 cm) is soaked for ten minutes in a dilute ethanolic solution of a long-chain organic compound, HS—$(CH2)_{10}$—COOH (Aldrich, 45,056-1) and then allowed to air-dry. The organic acid forms a SAM insulating layer between the conducting aluminum foil and an enzyme layer is formed by soaking the SAM-coated foil in a 50 microgram/milliliter solution of lysozyme for twenty minutes. The foil is soaked briefly in a glucose/ NaCl solution and allowed to air dry. The foil is cut into 0.25 cm×4 cm pieces and inserted into UHT milk container packaging so as to allow one side to contact the milk, while the other side remains exposed to the outside. The induced emf generated in the foil by the moving lysozyme molecules is measured by contacting the outside of the sensor with two probes of a digital voltmeter that has 1000 mega-ohm resistance between the two contacting electrodes (MDMV0100, Red Lion, York, Pa., USA). A background value is recorded for fresh milk. Sterile milk is tested after insertion into its packaging, and when the absolute value of the voltage increases (it can become more positive or more negative) in response to increased motion of lysozyme, the milk is rejected as not being sterile (for lysozyme motions in the presence of substrate, see Radmacher, et al. *Science* 265:1577–1579 (1994)).

EXAMPLE 2

Aluminum foil was soaked in an aqueous solution of parahydroxybenzoic acid, rinsed in water, and then soaked in a dilute solution of three distinct antibodies (Biodesign, Kennebunk, USA, catalogue numbers C11016M, C65310M, and C11018M) that recognize the pathogenic *E. coli* strain 0157:H7. The completed sensor sheet was cut into strips, and sensor strips were contacted to food samples (ground beef homogenized in phosphate buffer) so that one end contacted the ground beef solution while the other end was available for contact by the passive leads of a detection unit. When the particular *E. coli* strain was added to beef samples there was a significant increase in the induced emf recorded as a voltage over a resistor placed between two leads of a hand-held detector unit (as per the embodiment in FIG. 7). Background values in the absence of the *E. coli* cells (but other bacteria present) were 5.5 millivolts. When *E. coli* was present at 1–10 cells per milliliter, readings went over 200 millivolts (the off-scale of this detector system). All reading times were less then two minutes. Sensor strips from the same production batch were utilized in the identification of *E. coli* 0157:H7 in a water-diluted stool sample from a patient diagnosed as suffering from food poisoning. Sensor strips for Campylobacter, Salmonella and Listeria did not show above-background readings when contacted with diluted stool samples.

EXAMPLE 3

Aluminum foil (Reynolds) was soaked in a water solution of parahydroxybenzoic acid, rinsed in water, and then soaked for an hour in an antibody specific for the human pathogen, *Helicobacter pylori* (Biodesign, B65660R). The completed sensor foils were dried and then cut into strips 0.25 centimeter in width. Stomach biopsies from thirty-seven patients were placed in separate Eppendorf 1.5 milliliter tubes that contained approximately 0.5 milliliter of sterile saline solution. Sensor strips were cut to approximately 5 centimeters in length. Half of a strip was placed inside the Eppendorf tube, and the tube was closed. The sample was shaken and the portion of the strip outside of the tube was contacted at two points with the leads of a digital voltmeter (with a high internal impedance). Thirty-one positive cases were detected (average induced emf: 398 millivolts) and six negative cases were reported (average induced emf. 2.5 millivolts). The results were scored against other *H. pylori* detection methods including urease detection and pathological analysis.

EXAMPLE 4

Aluminum foil (10 cm×10 cm) was soaked in a solution of 4,4'-biphenyldicarboxylic acid (Aldrich, 22,526-6). The terminal carboxyl group of the SAM is negatively charged and was used to chelate iron ($Fe^{3+}$) delivered through a second soaking step in an aqueous solution of ferric hydroxide polymraltose complex (locally purchased). The positive Fe ions were then used to coordinate a DNA sample of oligothymidylic acid, $d(pT)_8$ (Sigma, O9010). The sensor strip thus consisted of "foil-SAM-Fe-DNA single strand $d(pT)_8$". The sensor strip has been used to identify the general presence of DNA in samples. Note that in this case, the DNA single strand is bound to the base member in a manner that leaves it parallel to the base member (due to Fe-phosphate interactions). One can also bind one end (3' or 5') of the nucleic acid so as to have it standing perpendicular to base member. Binding chemistries similar to those described in Example 9 below are appropriate for immobilization. Inert polyelectrolytes can be added to fill-in uncovered binding sites on the base member. A sample is placed in a 1.5 milliliter Eppendorf tube and half of a 5 centimeter long sensor strip (0.25 cm diameter) is placed inside the Eppendorf tube. The tube is closed and the solution shaken in order to contact solution to the sensor strip. If no DNA is present, induced current readings taken by contacting the leads of a voltmeter-based detection unit (as per the embodiment in FIG. 7) to the exposed strip are less than 20 millivolts (absolute value). If DNA is present and there is interaction with the binding agent, then the readings are in the hundreds of millivolts (absolute value). The specific score depends on the size of the resistor (775) placed between the electrodes connected to the detection unit.

EXAMPLE 5

A sensor was prepared as in Example 3, but the enzyme acetylcholine esterase (Sigma, C-2629) served as the macromolecular binding agent. Sensor strips were again placed in Eppendorf tubes. A solution of nerve agent was placed at the base of the Eppendorf tube, and there was no contact between the strip and the agent. Vapors from the chemical nerve agent reached the strip and induced emf values as high as 700 millivolts were recorded by a digital multimeter (with high internal impedance) contacting the strips at two points on the outside of the sealed Eppendorf tube. Detection of the nerve agent in gas form demonstrates the efficacy of the sensor as a poison gas monitor; binding of organic phosphate molecules ostensibly caused inhibition of the immobilized enzyme. There is a concomitant change in the enzyme structure (Dziri, et. Al. *Langmuir* 14: 4853–4859 (1998)) and a large voltage (as per the embodiment of FIG. 7) is recorded in response to the wholesale changes in electrostatic profile for the enzyme macromolecules. An audible or visual alarm could be made to sound to alert the wearer of such a device that poison gas is present.

EXAMPLE 6

A sensor was prepared for use in antibiotic residue testing. Penicillinase (Sigma, P0389) was the macromolecular binding agent and was physically absorbed onto aluminum foil coated with a SAM layer (parahydroxybenzoic acid). The foil was soaked in sodium chloride and glucose in order to further stabilize the bound enzyme molecules and render the enzyme available for sensing in milk. Sensor strips were cut into 15 cm×0.25 cm pieces. Strips were further cut down to 5 centimeter length prior to use. Antibiotics (penicillin G; amoxicillin; cloxicillin; dicloxicillin; cephapirin; cephalexin; ampicillin; cephasporin C—all purchased from Sigma) were prepared as separate stock solutions in water and diluted serially to parts-per-billion concentrations in skim, pasteurized milk. Samples of milk containing a given antibiotic were placed in Eppendorf tubes or disposable plastic vials. Sensor strips were contacted to the milk samples, and the leads of a digital multimeter with high internal impedance were contacted at two exposed (dry)positions on the sensor. Scores were recorded. Milk without antibiotics gave readings of 13 millivolts; samples tainted with one of the eight antibiotics showed readings from 150–250 millivolts (at FDA-mandated parts-per-billion cut-off values for the antibiotics in question).

EXAMPLE 7

Aluminum foil was soaked in an ethanolic solution parahydroxybenzoic acid, rinsed in water, and then soaked in an aqueous solution of antibodies, each capable of binding one of the following food-related pathogens: Salmonella, Listeria, *E. coli* 0157:H7, and Campylobacter. The foil was soaked in an aqueous solution of sucrose and sodium chloride and then allowed to air-dry. Sensor strips were cut to 0.5 cm×1.5 cm and attached to disposable containers such that a portion of the strip was inside the container and the remainder was exposed. A sensor strip may be exposed to water in the closed container, and a background reading may be measured by passively contacting exposed sensor strip at two positions with leads of a digital multimeter (Radio Shack, described previously). Induced current may be recorded as a voltage measured over a 150 kilo-ohm resistor placed in parallel with respect to the sensor strip. Food samples may be added to the water, the mixture shaken, and then new readings taken. If one or more of the target pathogens is present, a significant increase in voltage will be recorded. The food sample will be known to have a dangerous pathogen present.

EXAMPLE 8

Commercially-available aluminum foil (Reynolds, 10 cm×10 cm) is sprayed with an aqueous solution of parahydroxybenzoic acid (1 mM). The foil is rinsed in water, cut into several pieces and then soaked in separate aqueous solutions that each contain an antigen associated with one of the following viruses: HIV I, HIV II, HTLV I, HTLV II, Hepatitis B, Hepatitis C. After a twenty minute soak, the sensor sheets (foil-SAM-antigen) are separately soaked for ten minutes in solutions of glucose/NaCl and then allowed to dry in air. Sensor strips are cut to 0.25 cm×1.5 cm size and used in analyzing whole blood samples for the presence of antibodies for the aforementioned viruses. The sensor strips (one for each antigen) are placed partly inside a 1.5 milliliter disposable tube and contacted to saline. Background readings are recorded for each strip by a detection unit. A drop of blood is added to the tube, the sample shaken in order to afford contact between the blood and the strips, and levels of induced electromotive force are determined for each base member. Significant changes in signal frequency in a given sensor strip signals the presence of antibodies to the viral antigen associated with that particular strip. Alternatively, all of the viral antigens may be immobilized on a single sheet of SAM-coated foil. The foil (after packaging coat application)is cut into strips and single strips are placed between the barrel and needle of a disposable syringe. The syringe-sensor units are sterilized and then used to analyze blood taken up in the syringe. Changes (relative to a predetermined background) in induced current, emf, impedance, resistance, signal sign, frequency, or the like indicate that antibodies have bound to immobilized antigens. The implication is that antibodies to at least one of the relevant viruses are present in the blood.

EXAMPLE 9

A piece of polyethylene (PE) is placed in an oxygen plasma or a UV-ozone cleaner. The effect is to oxidize the hydrophobic, inert PE surface and to make it amenable to further chemical manipulations. The oxidized PE is exposed to the vapors of silicon tetrachloride ($SiCl_4$) and then water vapors. This process is repeated until the sample is shown to be fully hydrophilic ("wetted" as measured by a near-zero contact angle value of water on the modified PE surface). Several iterations of $SiCl_4/H_2O$ treatments may be required for preparation of PE with a chemically-bonded $SiO_2$ layer on its surface.

The modified PE sample is then exposed to the vapors of a boiling solution of isopropanol, water, and the compound $(CH_3O)_3$—Si—$(CH_2)_3$—SH. This compound will create a "siloxane" network (—Si—O—Si—) between the modified surface of the PE and the compound. The PE emerging from this solution is cured in an oven. The process of subjecting the PE to the compound $(CH_3O)_3$—Si—$(CH_2)_3$—SH and heating is repeated twice again. The resultant product is a PE with a thiol (—SH) terminated SAM surface wherein the thiol groups face upwards and away from the PE.

The thiol-terminated PE is placed in a commercially-available electroless silvering solution and removed. A 40 nm silver (Ag) layer is thereby deposited on the PE. (Note that silver binds very tightly to the thiols on the surface of the PE). This PE-Ag is immediately placed in an ethanolic solution of a compound with the general formula HS—R—OH and 11-mercaptoundecanoic acid (11-MUA) in a 10:1 (HS—R—OH: 11-MUA) ratio. The former compound serves the following two fuctions:

(1) the pendant hydroxyl group (—OH) serves to hydrate the macromolecules on the sensor surface and provide stability to the macromolecules in a non-aqueous environment because the hydroxyl group is very similar to water; and (2) the R group is chosen to balance insulation and electrical connectivity between the silver and the macromolecular binding agents. R is chosen to be a phenyl group or the $(CH_2)_6$ moiety when 11-MUA is used.

The latter compound, 11-MUA, allows for enzyme immobilization.

The 11-MUA is further modified in an aqueous solution of 1-ethyl-3-{3-(dimethylamino)propyl} carbodiimide hydrochloride (EDC) and N-hydroxysuccinimide (NHS). These compounds modify the 11-MUA and make it quite reactive to neutral amino ($NH_2$) groups that are present on all proteins or phosphate groups on the termini of nucleic acids. The incubation is for approximately ten minutes.

The sensor sheet in this Example is then soaked in the appropriate dilute glucokinase solution at neutral to slightly basic pH (one-half hour) to effect enzyme coupling to the modified PE-Ag surface through binding of lysine amino groups and the functionalized MUA. The sensor sheet is removed from the macromolecule solution and sonicated in an aqueous sodium chloride and sucrose solution to remove loosely-bound enzyme molecules. The sensor now has the following arrangement:

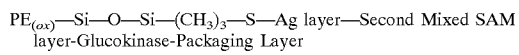

$PE_{(ox)}$—Si—O—Si—$(CH_3)_3$—S—Ag layer—Second Mixed SAM layer-Glucokinase-Packaging Layer Finally, sensor strips are cut to size and contacted to the leads of a detection unit appropriate for measuring the current induced by the motion of glucokinase in the presence of glucose. Typically, the electrodes will be contacted at two different positions on the silver surface. The device is now ready for use in glucose monitoring for diabetic patients.

EXAMPLE 10

Commercial aluminum foil is treated with a mixture (ratio of 1:10) of 4-carboxy-benzoic acid and parahydroxybenzoic acid. The SAM layer is next treated with 1-ethyl-3-{3-(dimethylamino)propyl} carbodiimide hydrochloride (EDC, Sigma E-1769) and NT-hydroxysuccinimide (NHS, Aldrich, 13067-2) ) in order to convert the exposed carboxy group of 4-carboxy-benzoic acid to a functionality (NHS ester) that is very reactive to protein amine groups and nucleic acid terminal phosphate groups. Addition of a dilute solution of binding agent(s) leads to rapid immobilization of the binding agent to the SAM-modified aluminum foil. A packaging layer is deposited by spraying the foil with an aqueous solution of sodium chloride and sucrose. The aluminum foil sheets are allowed to dried, and then they are cut into sensor strips for use in analyte detection. A strip is placed between the barrel and needle of a disposable syringe. As blood is drawn from a patient, the packaging layer is dissolved and the immobilized binding agents are brought into direct contact with the blood sample. If target analytes are present (possibly bacterial toxins), they interact with the bound macromolecules, and there is an increase in the amount of electrostatic material near the base member. Fluctuations of larger electrostatic fields implies fluctuation of larger magnetic fields, and there is a corresponding increase in induced electron motion in the base member. If a voltmeter-based detection unit is selected (as in the embodiment of FIG. 7), it may be contacted via electrodes at two exposed points on the aluminum foil base member. An appropriate resistor is placed between the electrodes within the detection unit so as to allow for an easily measurable signal. The detection of signals above a predetermined baseline value in the digital readout of the voltmeter signals that an analyte of interest is present. In the case when the analyte is a dangerous material or pathogen, an alarm is activated to warn of the potential health hazard. Several such foil strips, each one specific for a different pathogen, can be grouped to make a multiplexed system for multiple analyte detection or system redundancy.

EXAMPLE 11

A deoxyribonucleic acid single strand polymer of 200 bases is physically absorbed to silver-coated plastic disposable container. The silver is deposited on the plastic disposable tube by coating the plastic with silver ink (Jelt, Jeltargent). Silver ink is deposited so as to guarantee electrical connectivity between the silver or inside and outside of the tube. The deposited silver acts as base member in this example. A blood sample taken from a patient is exposed to the immobilized nucleic acid binding agent of the sensor strip. The binding of viral RNA to the immobilized complementary single-strand DNA is detected by a detection unit that detects an induced current flowing in a circuit that contains the exposed portion of the silver base member. The detection unit displays a visual alarm that virus has been detected when the current reading (in microamperes) passes a predetermined threshold.

EXAMPLE 12

Human receptor molecules are immobilized along the electrically-conductive lanes of a highly-parallel microfluidic analytic chip. The receptors are the macromolecular entities, while the lanes serve as multiple base members. Chemical products of a combinatorial library are sequentially exposed to the immobilized macromolecules (receptor), and a computer (880 in FIG. 8) monitors for interaction between the chemicals and the receptor molecules. Interactions that lead to altered induced emf readings (relative to background in absence of chemicals) in one or more base member units (820–823 in FIG. 8) are noted, and the corresponding chemicals are selected as lead compounds in the synthesis of ligands for this target receptor. A 200-lane system that allows for ninety seconds of interaction for each chemical with macromolecules allows for screening of 192,000 chemicals per twenty-four hours.

While the sensing strip architecture of "base material-SAM-macromolecule" has been described previously, analyte detection based on electromagnetic induction in a conducting base member is new in the art. Prior-art sensors require applied electrical signals and generally rely on the chemical generation of charged species near the sensor surface. Today, there are neither aluminum foil-based sensor strips (as described in the Examples above) nor sensor strips designed exclusively for the detection of an induced emf or induced current in a conducting base member. Thus, any sensor strip designed for the detection of an induced current btween two points of a conducting or low-resistivity semi-conducting base member as a funciton of analyte interation with the macromolecular binding agent immobilized on said strip would be produced and used with the express purpose of violating the invention described in this patent application. Such strips would find application in food pathogen detection, medical diagnostics, poison gas detection, and the like, while the detection units would constitute separate components.

The present invention has been described with a certain degree of particularity, however those versed in the art will readily appreciate that various modifications and alterations may be carried out without departing from the spirit and scope of the following claims: Therefore, the embodiments and examples described here are in no means intended to limit the scope or spirit of the methodology and associated devices related to the present invention.

What is claimed is:

1. A sensor (100) for detecting an analyte, comprising:
a base member (120) having a conductive electrical property;
at least one macromolecular entity (140) bound to said base member (120); CHARACTERIZED IN THAT
said macromolecular entity (140) and said base member (120) define an externally unpowered sensor strip, said macromolecular entity (140) being interactive at a level of specificity with a predetermined analyte (150), wherein an electrical signal is generated in said sensor strip responsive to presence of the analyte (150); and
a detection unit (170) passively coupled to said sensor strip for detecting said generated electrical signal.

2. The sensor according to claim 1, further comprising a self-assembled monolayer (130) bound to said base member (120) and proximate said macromolecular entity (140).

3. The sensor according to any of claims 1 or 2, wherein said macromolecular entity (140) comprises a first macromolecular entity (340) capable of interacting at a first specificity and a second macromolecular entity (345) capable of interacting at a second specificity for the detection of at least one analyte.

4. The sensor according to any one of claims 1, 2, or 3, wherein electrical leads (160) of said detection unit (170) are coupled to said sensor strip at no more than two positions (165, 167) of the sensor strip.

5. The sensor according to any one of claims 1, 2 or 3, further comprising tow equipotential leads (160) coupling said sensor strip to said detection unit (170).

6. The sensor according to any one of claims 1, 2 or 3, wherein the base member (120) is a conducting foil, coating, thin-film, ink, or solid piece.

7. The sensor according to claim 3, wherein said macromolecules (340,345) are arranged in a multilayer (341, 342) proximate the base member (120).

8. The sensor according to any one of claims 1, 2 or 3, further comprising a packaging layer (650) disposed above said macromolecular entity (640), said packaging layer being soluble in a medium that contains the analyte (655, 657).

9. A method for detecting an analyte, comprising the steps of:
(1) providing an electrically conductive base member (120);
(2) immobilizing at least one macromolecule (140) in proximity to said base member (120), wherein said macromolecule (140) is capable of interacting at a level of specificity with a predetermined analyte (150), CHARACTERIZED IN THAT
said base member (120) and said macromolecule (140) define an externally unpowered sensor strip;
exposing analyte to said macromolecule (140); and
detecting an electrical signal generated in said sensor strip, said electrical signal being responsive to analyte presence.

10. The method according to claim 9, further comprising the steps of:
(1) binding a self-assembled monolayer (130) to said base member (120); and
(2) immobilizing said macromolecule (140) proximate said self-assembled monolayer (130).

11. The method according to any one of claims 9 or 10, wherein said macromolecule (140) comprises a first macromolecule (340) capable of interacting at a first specificity and a second macromolecule (345) capable of interacting at a second specificity for the detection of at least one analyte.

12. The method according to any one of claims 9, 10 or 11, wherein said step of detecting is performed by equipotentially coupling a detection unit (170) to said sensor strip at no more than two positions (165, 167) of the sensor strip.

13. The method according to any one of claims 9, 10 or 11, wherein electrical leads (160) of a detection unit (170) are passively coupled to said sensor strip.

14. The method according to any one of claims 9, 10 or 11, wherein the base member (120) is a conducting foil, coating, thin-film, ink, or solid piece.

15. The method according to claim 11, wherein said macromolecules (340, 345) are arranged in a multilayer (341, 342) proximate the base member (320).

16. The method according to any one of claims 9, 10, or 11, further comprising the step of disposing a packaging layer (650) above said macromolecules (640), said packaging layer being soluble in a medium that contains the analyte (655, 657).

17. The method according to claim 13, further comprising the step of coupling said electrical leads (160) to a load for delivery of power thereto.

\* \* \* \* \*